(12) United States Patent
Yost et al.

(10) Patent No.: US 10,730,928 B2
(45) Date of Patent: Aug. 4, 2020

(54) BIOFABRICATION TECHNIQUES FOR THE IMPLEMENTATION OF INTRINSIC TISSUE GEOMETRIES TO AN IN VITRO COLLAGEN HYDROGEL

(71) Applicants: University of South Carolina, Columbia, SC (US); MUSC Foundation for Research Development, Charleston, SC (US)

(72) Inventors: Michael John Yost, Mt. Pleasant, SC (US); Veronica Rodriguez-Rivera, Charleston, SC (US)

(73) Assignees: University of South Carolina, Columbia, SC (US); MUSC Foundation for Research Development, Charleston, SC (US)

( * ) Notice: Subject to any disclaimer, the term of this patent is extended or adjusted under 35 U.S.C. 154(b) by 433 days.

(21) Appl. No.: 15/514,091

(22) PCT Filed: Sep. 28, 2015

(86) PCT No.: PCT/US2015/052633
§ 371 (c)(1),
(2) Date: Mar. 24, 2017

(87) PCT Pub. No.: WO2016/049625
PCT Pub. Date: Mar. 31, 2016

(65) Prior Publication Data
US 2017/0247430 A1    Aug. 31, 2017

Related U.S. Application Data

(60) Provisional application No. 62/055,688, filed on Sep. 26, 2014.

(51) Int. Cl.
| | | |
|---|---|---|
| *C07K 14/78* | (2006.01) |
| *C07K 14/76* | (2006.01) |
| *C08L 89/06* | (2006.01) |
| *C08H 1/06* | (2006.01) |
| *D01D 1/02* | (2006.01) |
| *D01F 11/02* | (2006.01) |
| *D01D 5/00* | (2006.01) |
| *A61L 27/24* | (2006.01) |
| *C08H 1/02* | (2006.01) |
| *D01F 4/00* | (2006.01) |

(52) U.S. Cl.
CPC .............. *C07K 14/78* (2013.01); *A61L 27/24* (2013.01); *C07K 14/76* (2013.01); *C08H 1/02* (2013.01); *C08H 1/06* (2013.01); *C08L 89/06* (2013.01); *D01D 1/02* (2013.01); *D01D 5/0046* (2013.01); *D01D 5/0061* (2013.01); *D01F 4/00* (2013.01); *D01F 11/02* (2013.01); *D10B 2211/06* (2013.01)

(58) Field of Classification Search
CPC ..................................................... A61L 27/24
See application file for complete search history.

(56) References Cited

U.S. PATENT DOCUMENTS

| 5,385,606 | A | 1/1995 | Kowanko |
| 6,921,412 | B1* | 7/2005 | Black ................. A61L 24/0089 606/213 |
| 2002/0022588 | A1* | 2/2002 | Wilkie ................. A61L 24/001 424/94.64 |
| 2008/0038352 | A1 | 2/2008 | Simpson et al. |
| 2013/0231287 | A1 | 9/2013 | Nacharaju et al. |
| 2013/0280307 | A1 | 10/2013 | Fullana et al. |
| 2013/0337227 | A1 | 12/2013 | Tanaka et al. |

FOREIGN PATENT DOCUMENTS

WO    WO 2010/048281    4/2010

OTHER PUBLICATIONS

Ankam, et al. "Substrate topogaphy and size determine the fate of human embryonic stem cells to neuronal or glial lineage" *Acta Biomater.* 9(1) (2013) pp. 4535-4545.
Bose, et al. "Bone tissue engineering using 3D printing" *Materials Today* 16(12) (2013) pp. 496-504.
Burmeister, et al. "Glutaraldehyde cross-linked glutamate oxidase coated microelectrode arrays: Selectivity and resting levels of glutamate in the CNS" *ACS Chem Neurosci* 4(5) (2013) pp. 721-728.
Cao, et al. "A biodegradable porous composite scaffold of PGA/beta-TCP for bone tissue engineering" *Bone* 461(2) (2010) pp. 386-395.
Chan, et al. "Scaffolding in tissue engineering: general approaches and tissue-specific considerations" *Eur Spine J* 17(Suppl 4) (2008) pp. S467-S749.
Chatterji, P.R. "Gelatin with hydrophilic/hydrophobic grafts and glutaraldehyde crosslinks" *J of Appl Poly Sci* 37(8) (1989) pp. 2203-2212. (Abstract only).
Czajka, et al. "Self-Assembly of Prevascular Tissues from Endothelial and Fibroblast Cells under Scaffold-Free, Non-adherent Conditions" *Tissue Eng Part A* 21(1-2) (2014) pp. 277-287.
Drake, et al. "Action of proteolytic enzymes on tropocollagen and insoluble collagen" *Biochemistry* 5(1) (1966) pp. 301-392.
Freije, et al. "Chemically modified, immobilized trypsin reactor with improved digestion efficiency" *J Proteome Res* 4(5) (2005) pp. 1805-1813.

(Continued)

*Primary Examiner* — Robert J Yamasaki
*Assistant Examiner* — Stephen A Perkins
(74) *Attorney, Agent, or Firm* — Dority & Manning, P.A.

(57) ABSTRACT

Methods for reaction electrospinning are provided to form collagen fibers. The method can include: acidifying a collagen in an acidic solvent to form an acidic collagen solution; electrospinning the acidic collagen solution within an alkaline atmosphere (e.g., including ammonia vapor) to form collagen fibers; and collecting the collagen fibers within a salt bath (e.g., including ammonium sulfate). The acidic solvent can include water and an alcohol, and can have a pH of about 2 to about 4 (e.g., including a strong acid, such as HCl). An albumin rubber is also provided, which can include albumin crosslinked with glutaraldehyde.

3 Claims, 18 Drawing Sheets

(56) References Cited

OTHER PUBLICATIONS

Fürst, et al. "Release of glutaraldehyde from an albumin-glutaraldehyde tissue adhesive causes significant in vitro and in vivo toxicity" *Ann Thorac Surg* 79(5) (2005) pp. 1522-1529.
Guarino, et al. "Polylactic acid fibre-reinforced polycaprolactone scaffolds for bone tissue engineering" *Biomaterials* 29(27) (2008) pp. 3662-3670.
Habeeb, et al. "Reaction of proteins with glutaraldehyde" *Biochemistry and Biophysics* 126(1) (1968) pp. 16-26.
Harris, et al. "In vitro fibrillogenesis of collagen type I in varying ionic and pH conditions" *Micron* 49 (2013) pp. 60-68.
Hartman, et al. "Microfabricated electrospun collagen membranes for 3-D cancer models and drug screening applications" *Biomacromolecules* 10(8) (2009) pp. 2019-2032.
Hasan, et al. "Electrospun scaffolds for tissue engineering of vascular grafts" *Acta Biomater* 10(1) (2014) p. 11-25.
Hofman, et al. "Effects of the molecular format of collagen on characteristics of electrospun fibres" *J of Mat Sci* 47(3) (2011) pp. 1148-1155.
Holmes, et al. "Reconstitution of collagen fibrils in vitro; the assembly process depends on the initiating procedure" *International J of Biol Macro* 8(3) (1986) pp. 161-166.
Huang, et al. "A review on polymer nanofibers by electrospinning and their applications in nanocomposites" *Comp Sci Tech* 63(15) (2003) pp. 2223-2253.
Jeong, et al. "In vivo biocompatibilty and degradation behavior of elastic poly(Llactide-co-epsilon-caprolactone) scaffolds" *Biomaterials* 25(28) (2004) pp. 5939-5946.
Keech, M.K. "The effect of collagenase and trypsin on collagen-an electron microscopic study" *The Anatomical Record* 119(2) (1954) pp. 139-159. (Abstract only).
Khadka, et al. "Protein- and peptide-based electrospun nanofibers in medical biomaterials" *Nanomedicine* 8(8) (2012) pp. 1242-1262.
Kretlow, et al. "Injectable matrices and scaffolds for drug delivery in tissue engineering" *Adv Drug Deliv Rev* 59(4-5) (2007) pp. 263-273.
Kundu, et al. "Chapter 2—Biomaterials for Biofabrication of 3D Tissue Scaffolds" *Biofabrication* (2013) pp. 23-46.
Lemaire, et al. "Nerve and conduction tissue injury caused by contact with BioGlue" *J Surg Res* 143(2) (2007) pp. 286-293.
Liu, et al. "Nanofibrous collagen nerve conduits for spinal cord repair" *Tissue Eng Part A* 18(9-10) (2012) pp. 1057-1066.
Liu, et al. "Photochemical crosslinked electrospun collagen nanofibers: Synthesis, characterization and neural stem cell interactions" *J Biomed Mater Res A* 95(1) (2010) pp. 276-282.
Lundgren, et al. "Extracellular matrix components influence the survival of adult cardiac myocytes in vitro" *Exp Cell Res* 158(2) (1985) pp. 371-381.
MacKinnon, et al. "Electron microscopy study of refractory ceramic fibers" *Appl Occup Environ Hyg* 16(10) (2001) pp. 944-951.
Mason, et al. "Tuning three-dimensional collagen matrix stiffness independently of collagen concentration modulates endothelial cell behavior" *Acta Biomater* 9(1) (2013) pg. 4635-4644.
Masuelli, M.A. "Study of Bovine Serum Albumin Solubility in Aqueous Solutions by Intrinsic Viscosity Measurements" *Adv Phys Chem* 2013:360239 (2013) pp. 1-8.
Matthews, et al. "Electrospinning of Collagen Nanofibers" *Biomacromolecules* 3(2) (2002) pp. 232-238.
Migneault, et al. "Glutaraldehyde: behavior in aqueous solution, reaction with proteins, and application to enzyme crosslinking" *Biotechniques* 37(5) (2004) pp. 790-802.
Nugent, et al. "Tissue engineering therapy for cardiovascular disease" *Circ Res* 92(10) (2003) pp. 1068-1078.
Oh, et al. "Fabrication and characterization of hydrophilic poly(lactic-co-glycolic acid)/poly(vinyl alcohol) blend cell scaffolds by melt-molding particulate-leaching method" *Biomaterials* 24(22) (2003) pp. 4011-4021.
Peters, et al. "Albumin research in the 21st century" *Biochim Biophys Acta* 1830(12) (2013) pp. 5351-5353.
Prabhakaran, et al. "Electrospun nanostructured scaffolds for bone tissue engineering" *Acta Biomateriala* 5(8) (2009) pp. 2884-2893.
Reznikov, et al. "Three-dimensional structure of human lamellar bone: The presence of two different materials and new insights into the hierarchical organization" *Bone* 59 (2014) pp. 93-104.
Salerno, et al. "Tailoring the pore structure of PCL scaffolds for tissue engineering prepared via gas foaming of multi-phase blends" *Journal of Porous Materials* 19(2) (2011) pp. 181-188.
Sell, et al. "Electrospinning of collagen/biopolymers for regenerative medicine and cardiovascular tissue engineering" *Advanced Drug Delivery Reviews* 61(12) (2009) pp. 1007-1019.
Shih, et al. "Growth of mesenchymal stem cells on electrospun type I collagen nanofibers" *Stem Cells* 24(11) (2006) pp. 2391-2397.
Shin, at al. "Electrospinning: A whipping fluid jet generates submicron polymer fibers" *Applied Physics Letters* 78(8) (2001) pp. 1149-1151.
Silva, et al. "Chemical modifications on proteins using glutaraldehyde" *Food Technology and Biotechnology* 42(1) (2004) pp. 51-56.
Tanford, et al. "The Viscosity of Aqueous Solutions of Bovine Serum Albumin between pH 4.3 and 10.5" *The Journal of Physical Chemistry* 60(2) (1956) pp. 225-231.
Tobitani, et al. "The intrinsic viscosity of polyelectrolytes revisited" *Polymer International* 44(3) (1997) pp. 338-347.
Trelstad, et al. "Collagen fibrillogenesis: intermediate aggregates and suprafibrillar order" *Proc Natl Acad Sci USA* 73(11) (1976) pp. 4027-4031.
Vats, et al. "Scaffolds and biomaterials for tissue engineering: a review of clinical applications" *Clinical Otolaryngology* 28(3) (2003) pp. 165-172.
Whelan, et al. "Collagen I initiates endothelial cell morphogenesis by inducing actin polymerization through suppression of cyclic AMP and protein kinase A" *J Biol Chem* 278(1) (2003) pp. 327-334.
Yadav, et al. "Viscosity analysis of high concentration bovine serum albumin aqueous solutions" *Pharm Res* 28(8) (2011) pp. 1973-1983.
Yang, et al. "Mechanical properties of single electrospun collagen type I fibers" *Biomaterials* 29(8) (2008) pp. 955-962.
Zhang, et al. "Physicochemical properties of collagen, gelatin and collagen hydrolysate derived from bovine limed split wastes" *Journal of the Society of Leather Technologists and Chemists* 90(10) (2006) pp. 23-38.
Zheng, et al. "Biomimetic Collagen Nanofibrous Materials for Bone Tissue Engineering" *Advanced Engineering Materials* 12(9) (2010) pp. B451-B466.
Zhu, et al. "Ch.12: Biofabrication of Tissue Scaffolds" *Advances in Biomaterials Science and Biomedical Applications* (2013) pp. 315-328.
Abedi et al., "A Collagen-Poly(vinyl alcohol) Nanofiber Scaffold for Cartilage Repair", 2010, 11 pages.
Boonen et al. "The Muscle Stem Cell Niche: Regulation of Satellite Cells During Regeneration", Tissue Engineering: Part B, 14-4, 2008, pp. 419-431.
De Coppi et al., "Myoblast-Acellular Skeletal Muscle Matrix Construct Guaratee a Long-Term Repair of Experimental Full-Thickness Abdominal Wall Defects", Tissue Engineering, 12-7, 2006, pp. 1929-1936.
International Search Report and Written Opinion for PCT/2018/052633 dated Dec. 15, 2015, 11 pages.
Dong et al., "Electrospinning of Collagen Nanofibers Scaffold from Benign Solvents", Macromolecular Rapid Communication, 2009, pp. 539-542.
Dyer et al., "Sonic Hedgehog Maintains Proliferation in Secondary Heart Field Progenitors and is Required for Normal Arterial Pole Formation", Developmental Biology, 2009, pp. 91-98.
Estrela et al., "Mesenchymal Stem Cells in the Dental Tissues: Perspectives for Tissue Regeneration", Brazilian Dental Journal, 22-2, Brazil, pp. 91-98.
Evans et al., "Novel 3D Culture System for Study of Cardiac Nyocyte Development", American Journal of Physiology: Heart and Circulatory Physiology, 285-2, 2003, pp. H570-H578.
Fann et al., "A Model of Tissue-Engineering Ventral Repairs", Investigative Surgery, 2006, pp. 193-205.
Gilbert et al., "Substrate Elasticity Regulates Skeletal Muscle Stem Cell Self-Renewal in Culture", Sciencexpress, 2010, pp. 1-5.

(56) References Cited

OTHER PUBLICATIONS

Goodwin at al., "A Three Dimensional Model of Vasculogenesis", Developmental Dynamics, 2005, pp. 122-129.
Grefte et al., "Model for Muscle Regeneration Around Fibrotic Lesions in Recurrent Strain Injuries", Medicine and Science in Sports and Exercise, 42-4, pp. 813-839.
Gurtner et al., "Wound Repair and Regeneration", Nature, 2008, pp. 314-321.
Levenberg et al., "Engineering Vascularized Skeletal Muscle Tissue", Nature Biotechnology, 23-7, 2005, pp. 879-884.
Lincoln et al., "Molecular and Developmental Mechanism of Congenital Heart Valve Diseases", Birth Defects Research. A Clinical and Molecular Teratology, 91-6, 2011, pp. 526-534.
Lutolf et al., "Synthetic Biomaterials as Instructive Extracellular Microenvironments for Morphogenesis in Tissue Engineering", Nature Technology, 2005, pp. 47-55.
Madri et al., "Phenotypic Modulation of Endothelial Cells by Transforming Growth Factor-Beta Depends Upon Composition and Organization of the Extracellular Matrix", Journal of Cell Biology, 1988, pp. 1375-1384.
Montarras et al., "Direct Isolation of Satellite Cells for Skeletal Muscle Regeneration", Science, 2005, pp. 2064-2067.
Prestwich et al., "Bioartificial Stem Cell Niches: Engineering a Regenerative Microenvironment", Regenerative Nephrology, 2-11, pp. 245-255.
Propst at al., "Focused In Vivo Genetic Analysis of Implanted Engineering Myofascial Constructs", Journal of Investigative Surgery, 2009, pp. 35-45.
Robinson et al., "Extracellular Matrix Scaffold for Cardiac Repair", Journal of the American Heart Association, 2005, pp. 135-143.
Simpson et al., "Regulation of Cardiac myocytes Protein Turnover and Myofibrillar Structure In Vitro by Specific Direction of Stretch", Circulation Research, 85-10, 1999, pp. e59-e69.
Simpson et al., "Modulation of Cardiac Myocyte Phenotype In Vitro by the Composition and Orientation of the Extracellular Matrix", Journal of Cellular Physiology, 1994, pp. 89-105.
Snarr et al., "A Spatiotemporal Evaluation of the Contribution of the Dorsal Mesenchymal Protusion to cardiac Development", Developmental Dynamics, 2007, pp. 1287-1294.
Valarmathi et al., "A Three-Dimensional Tubular Scaffold That Modulates the Osteogenic Vasculogenic Differentiation of Rat Bone Marrow Stromal Cells", Tissue Engineering Part A, 2008, pp. 491-504.
Yost et al., "A Novel Tubular Scaffold for Cardiovascular Tissue Engineering", Tissue Engineering, 10-1/2, 2004, pp. 273-284.
Yost et al., "Tissue Engineered Heart Tube Using Embryonic Tissue", Microscopy and Microanalysis, 2005, pp. 1252-1253.
Zeugolis et al., "Electrospinning of Pure Collagen Nanofibers—Just an Expensive Way to Make Gelatin?", Biomaterials, 2008, pp. 2293-2305.

\* cited by examiner

FIG. 7

BIOFABRICATION TECHNIQUES FOR THE IMPLEMENTATION OF INTRINSIC TISSUE GEOMETRIES TO AN IN VITRO COLLAGEN HYDROGEL

PRIORITY INFORMATION

The present application claims priority to U.S. Provisional Patent Application Ser. No. 62/055,688 titled "Novel Biofabrication Techniques for the Implementation of Intrinsic Tissue Geometries to an in Vitro Collagen Hydrogel" of Yost, et al. filed on Sep. 26, 2014, the disclosure of which is incorporated by reference herein.

GOVERNMENT SUPPORT CLAUSE

This invention was made with government support under 1R01DE019355 awarded by the National Institutes of Health—NIDCR. The government has certain rights in the invention.

BACKGROUND

The tissue engineering field has created great demands for the next generation of biomaterials and biofabrication techniques. These materials and techniques need to provide simple and economical biomaterials that are cell instructive and suitable for transplantation. These materials must recreate and mimic the 3D in vivo niche and be able to provide the proper cues for the cells to migrate, proliferate, differentiate, promote angiogenesis, and ultimately direct the regeneration native tissue architecture. (Prestwich, Ghaly, Brudnicki, Ratliff, & Goligorsky, 2011).

Biomaterials generally fall into two categories, synthetic and naturally derived materials. Recent promising efforts have been made using primary cells in combination with synthetic matrices, such as PEG (Gilbert, et al., 2010), and poly(glycolic acid)(PGA)/poly-L-lactic acid (PLLA) (Levenberg, et al., 2005) (Boonen & Post, 2008) natural and synthetic hybrid materials such as collagen-poly(vinyl alcohol) (Abedi, Sotoudeh, Soleymani, Shafiee, Mortazavi, & Aflatoonian, 2010), naturally derived materials created from decellularization of native tissues (De Coppi, et al., 2006) and repolymerized naturally occurring extracellular matrix components such as collagen (Grefte, Kuijpers-Jagtman, Torensma, & Von Den Hoff, 2010; Yost, et al., 2004). These materials have been used somewhat successfully in the laboratory for cell culture, small and large animal in vivo testing, and to a very small extent human surgical transplantation. A common fabrication technique for these materials is the creation of the hydrogels. Hydrogels are polymeric materials that can retain large amounts of water without dissolving. There are several techniques commonly used to create these hydrogels which include chemical cross-linking, photo cross-linking, and sol-gel synthesis. Other hydrogels are formed through spinning, bioprinting or microfabrication process among other techniques (Prestwich, Ghaly, Brudnicki, Ratliff, & Goligorsky, 2011).

Tissue scaffolds plays a crucial role towards tissue regeneration process. The ideal scaffold has to fulfill several requirements such as the adequate composition, specific cell population, and well-defined architectural features. Scaffold created from natural biological materials provide ideal compatibility and functionality. Collagen is a natural and a major constituent of the extracellular matrix that contains the necessary biological information that directs the cell behavior (Yost, et al., 2004). Collagen Type I accounts for 70-90% of collagen in the body. Specific techniques need to be developed in order to reconstitute a collagen scaffold that will retain its mechanical properties and micro geometric features similar to the natural tissue, and induced in vivo cell behavior.

Novel 3D tubular collagen scaffold for cardiovascular tissue engineering have been successfully developed and commercialized using a counter rotating cone extrusion system, as disclosed in U.S. Pat. No. 7,338,517 of Yost, et al. and (Yost, et al., 2004), which are incorporated by reference herein. The device is capable of producing continuously spiraling alignment of the collagen fibers, which is seen in the layers of cardiac myocytes and extracellular matrix. This is an important key factor in vivo, because it provides the heart the ability to contract and move the blood from its ventricular cavity to the systematic vasculature. The collagen provided the biological information needed to direct cell behavior and along with the precise fiber orientation, the tube wall contracted spontaneously. The cardiac myocytes had developed an in vivo phenotype, possess aligned myofibers and developed sarcomeres. Furthermore, using this 3D tubular scaffold, Valarmathi et al. was able to induce the maturation and differentiation of BMSCs into vascular lineages, vasculogenesis, which was able to support microvessel morphogenesis.

One unique and unexpected aspect of this engineered scaffold is that it promoted the expression of an in vivo like phenotype and tissue organization for many cell types. (Yost, et al., 2004; Evans, Sweet, Price, Yost, & Goodwin, 2003; Valarmathi, Yost, Goodwin, & Pott, 2008; Goodwin R. L., Nesbitt, Price, Well, Yost, & Potts, 2005). The tube scaffold has been used to study embryonic and (Yost, et al., 2004; Goodwin R. L., Nesbitt, Price, Wells, Yost, & Potts, 2005) neonatal cardiomyocytes, cardiac fibroblasts, coronary vasculogenesis, and development of tissue-engineered cardiac valves (Evans, Sweet, Price, Yost, & Goodwin, 2003; Yost, Franchini, Goodwin, Nesbitt, & Price, 2005). We have also used our scaffold to regenerate skeletal muscle in a rat hernia model (Fann, Terracio, Yan, Franchini, & Yost, 2006). The tube has been combined with satellite cells and used to study angiogenesis and inflammation on a molecular level in vivo during skeletal muscle repair (Propst, et al., 2009).

During the course of these investigations, it was realized that the next generation of fabrication technology was needed to create collagen scaffold with branch points and more intricate, in vivo like geometries. The approach mimics early morphogenesis, based on the realization that both genes and physical forces regulate self-assembly and 3-dimensional pattern formation of complete tissues.

Not only is the 3D structure necessary for vasculogenesis but so is the composition of the substrate. Previous studies have shown that the formation of endothelium-lined tubular structures was promoted in vitro by the presence of laminin in the matrix (Madri, Patt, & Tucker, 1988). In a pure collagen type I, there was a delay in the promotion of endothelial cells to enhance tubulogeneis (Madri, Patt, & Tucker, 1988).

Although this technology provides the ability to re-create the in vivo architecture and vasculogenesis of BMSCs in the extracellular matrix, it has some limitations: specifically, it doesn't replicate the complex geometries and architectures found in in vivo tissues. The interaction of the cells with a specific arrangement and structure of the in vivo niche are vital to provide the necessary cues for the development of in vivo phenotypes. (Yost, et al., 2004).

As such, a need exists for methods of re-creating the in vivo architecture and vasculogenesis of BMSCs in the extracellular matrix while replicating the complex geometries and architectures found in in vivo tissues. For example, the next generation of fabrication technology is currently needed to create a collagen scaffold with branch points and more intricate, in vivo like-geometries.

SUMMARY

Objects and advantages of the invention will be set forth in part in the following description, or may be obvious from the description, or may be learned through practice of the invention.

Methods are generally provided for reaction electrospinning to form collagen fibers. In one embodiment, the method includes: acidifying a collagen in an acidic solvent to form an acidic collagen solution; electrospinning the acidic collagen solution within an alkaline atmosphere (e.g., including ammonia vapor) to form collagen fibers; and collecting the collagen fibers within a salt bath (e.g., including ammonium sulfate). The acidic solvent can include water and an alcohol, and can have a pH of about 2 to about 4 (e.g., including a strong acid, such as HCl).

An albumin rubber is also generally provided, which can include albumin crosslinked with glutaraldehyde.

Methods are also generally provided for forming an albumin rubber. In one embodiment, the method includes adding glutaraldehyde to an albumin serum, wherein the albumin serum comprises proteins having an amino functional group; and crosslinking the glutaraldehyde with the amino functional group of the proteins to form the albumin rubber.

Methods are also generally provided for forming an engineered bio-scaffold. In one embodiment, the method includes: filling a mold with an albumin rubber such that the albumin rubber conforms to the shape of the mold; removing the albumin rubber from the mold to form a rubber blank; coating the rubber blank with collagen such that the collagen takes the shape of the rubber blank; and selectively removing the rubber blank from the inside of the collagen to form the bio-scaffold.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 7 shows a schematic of an exemplary electrospinning technique. In our lab, the electrospinning setup was built that contained all the necessary components for controlling the fiber production.

FIGS. 10a-10d show one of the slices:

FIG. 10a highlighted portions correspond to DAPI (nuclear stain);

FIG. 10b highlighted portions correspond to phalloidin (f actin stain) composing the cytoskeleton of the cells;

FIG. 10c highlighted portions correspond to the SMA (smooth muscle actin) which will bind to a actin, with a significant expression of a actin indicating the presence of vasculature smooth muscle cell; and FIG. 10d shows all of these highlighted portions together.

DETAILED DESCRIPTION OF INVENTION

Figure 1:
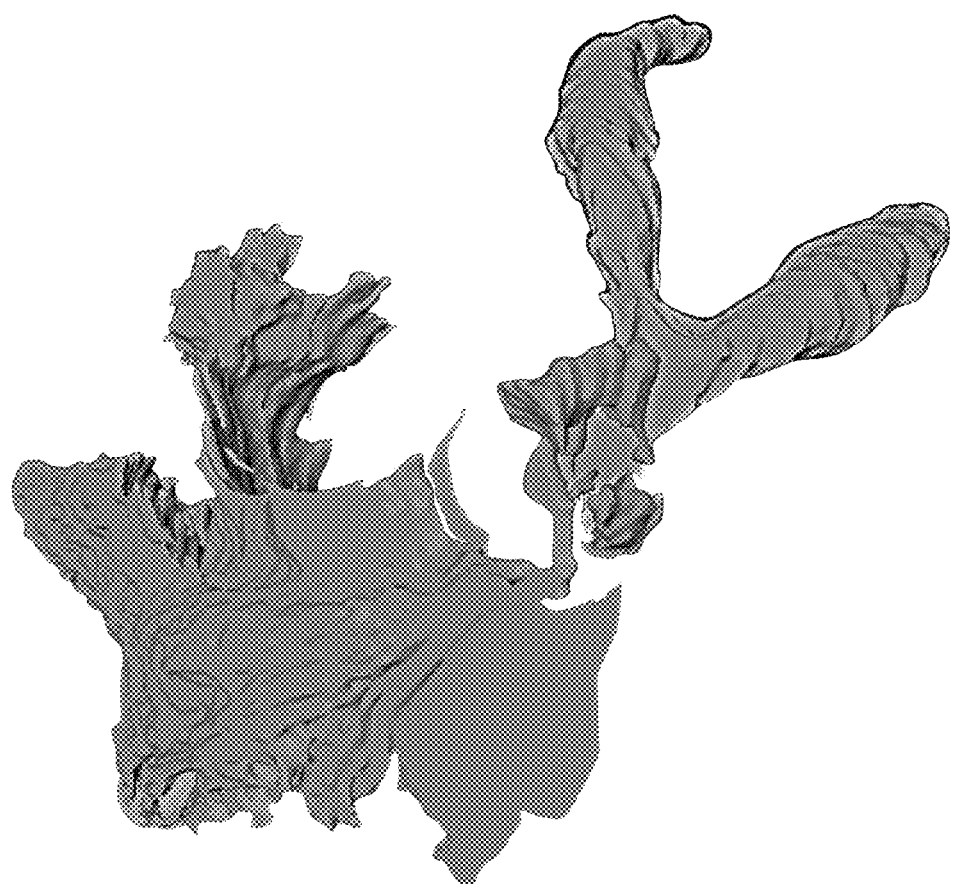
FIG. 1 shows an Amira® model for stage 40 embryonic heart. High-resolution images were taken from the sliced of the sectioned heart at stage 40. The green area represents the lumen of the right ventricle and the yellow area represent the lumen of the pulmonary truck as it branches to each bronchus.

The following description and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the following description is by way of example only, and is not intended to limit the invention.

A novel biofabrication technique is generally provided that combines state of the art imaging, 3D printing, and selective enzymatic activity to create the new generation of biomaterials for research and clinical application. A key aspect of this work is the development and characterization of a new mold system, which is referred to herein as "BSA rubber." This material allows the adequate transfer of the specific architectural features to a natural scaffold material. According to the Examples below, a prototype was formed that included a 3D collagen scaffold with 4 and 3 mm channels which represents a branched architecture.

Biomaterials that recapitulate the intrinsic architecture of in vivo tissue are vital for study diseases, as well as to facilitate the regeneration of lost and malformed soft tissue. Platform biofabrication technology is generally provided that can be tuned to mimic the native in vivo architecture and geometries vital to the physiological function of the tissues. Without wishing to be bound by any particular theory, it is currently believed that cell behavior is regulated in part by the composition, modulus and geometric features of its specific micro-environment. Thus, a manufactured micro environment must incorporate geometric features on the same length scale as native tissues. As such, the novel biofabrication technique has been developed that combines state of the art imaging, micromachining, and selective enzymatic activity to create the new generation of biomaterials for research and clinical application. These materials have a true three dimensional architecture and are created with flow channels or tissue voids that truly represent the in vivo niche. For example, a 3D branched vessel using type I collagen can be developed, in which either vascular endothelial cells or pluripotent bone marrow stromal cells are cultured. These cells can be cultured both on the exterior surface of the biomaterial as well as within the interior channels and voids. This fabrication technology along with tunable biomaterials can facilitate the regeneration of lost or malformed soft tissues. These new biomaterials and technologies will enable the modulation of cell potential, and thus, accelerate discovery in the field of regenerative medicine.

I. Image Distinct Tissue Geometries and Convert to Machine G Code

Microscopy can be used to collect 3D images of the tissue geometries of interest. For example, confocal or other suitable microscopy can be utilized to collect z-stack (collections of 2D images that can be used to recreate 3D models) images of the tissue geometries of interest. Any suitable tissues can imaged and a mold created, including but art not limited to a heart, a kidney (e.g., with a branched vascular tree), etc. From these tissues, the necessary architecture details can be obtained to demonstrate the technology and generate the G-code (machining language) in order to create 3D model that represents the in vivo tissue.

A commercial software package, Amira®, can then be utilized to reconstruct the flow paths and channels of such tissues. Then, the images can be converted to machine G-code language using commercial software (e.g., Mastercam Art® or other techniques to bring the 3D image into MasterCAM®). A milling machine (e.g., Microlution 363-S micro milling machine) can then use the G-code to machine these features into stainless steel molds of the tissue geometry.

In one embodiment, the software is run on a computer or other suitable processing unit. Generally, the software may include suitable computer-readable instructions that, when implemented, configure the computer to perform various different functions, such as receiving, transmitting and/or executing the images into the milling maching.

A computer generally includes a processor(s) and a memory. The processor(s) can be any known processing device. Memory can include any suitable computer-readable medium or media, including, but not limited to, RAM, ROM, hard drives, flash drives, or other memory devices. Memory stores information accessible by processor(s), including instructions that can be executed by processor(s). The instructions can be any set of instructions that when executed by the processor(s), cause the processor(s) to provide desired functionality. For instance, the instructions can be software instructions rendered in a computer-readable form. When software is used, any suitable programming, scripting, or other type of language or combinations of languages may be used to implement the teachings contained herein. Alternatively, the instructions can be implemented by hard-wired logic or other circuitry, including, but not limited to application-specific circuits.

Memory can also include data that may be retrieved, manipulated, or stored by processor(s). For instance, after receiving the temperature measured from the pyrometer, memory can store the temperature information. Additionally, memory can store reference temperatures for various substrate materials and/or powder materials.

The computing device can include a network interface for accessing information over a network. The network can include a combination of networks, such as Wi-Fi network, LAN, WAN, the Internet, cellular network, and/or other suitable network and can include any number of wired or wireless communication links. For instance, computing device could communicate through a wired or wireless network with imaging and/or milling maching.

The approach mimics early morphogenesis, based on the realization that both genes and physical forces regulate self-assembly and 3-dimensional pattern formation of complete tissues. As can be seen in our preliminary data, confocal microscopy and other high resolution imaging techniques has been successful in collecting z-stack images that can be imported into the software.

II. Bovine Serum Albumin Rubber Fabrication

In many commercial fabrication systems, the creation of internal voids, channels and features are made using sand or other suitable removable material. The metal or plastic part is formed around the sand mold and once solidified the sand is removed. In much the same manner, the next generation of biomaterials needed the "biosand" equivalent. The presently described BSA rubber was developed as a substitute for biosand. The BSA rubber is a newly formulated material that comprises bovine serum albumin crosslinked with glutaraldehyde, and in certain embodiments, consists of bovine serum albumin crosslinked with glutaraldehyde.

Crosslinked BSA is trypsin labile and readily digested by the enzyme at mild pH and temperature conditions. Conversely, intact type I collagen is very resistant to trypsin digestion. These features can be utilized to selectively remove the BSA rubber leaving the collagen behind.

Figure 4A:
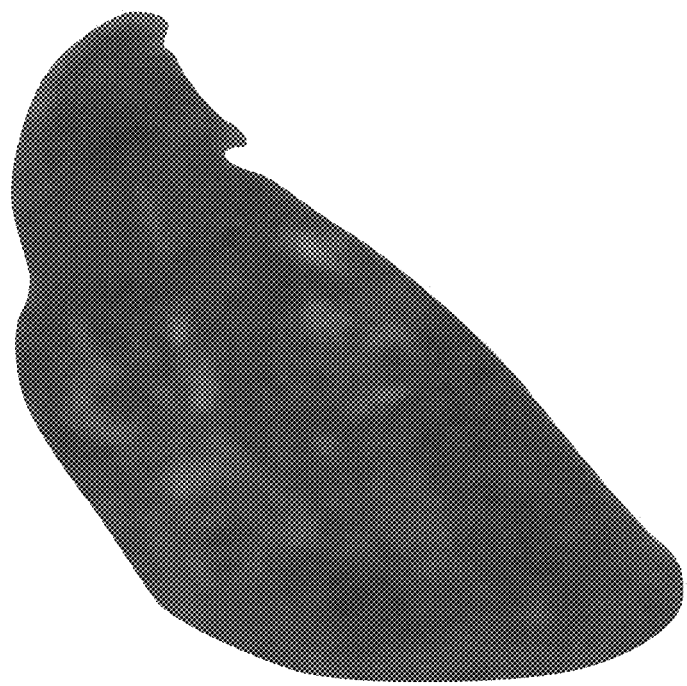
FIG. 4a shows BSA rubber according the Examples.

The rubber can be reaction injection molded into the intricate geometries of a tissue molds. The collagen can be formed around the rubber by the techniques described. FIG. 4a shows a piece of the BSA rubber casted in a 12 well plate. Creating precise dimension molds, the BSA rubber can be injected and obtained good consistency.

A crosslinked albumin rubber can be reaction injection molded into the intricate geometries of the tissue molds. The reaction conditions can be controlled to a) hold dimensions during scaffold creation; b) allow for minimum processing of selective enzyme digestion for removal; and c) minimize impact on collagen scaffold material.

Figure 11:
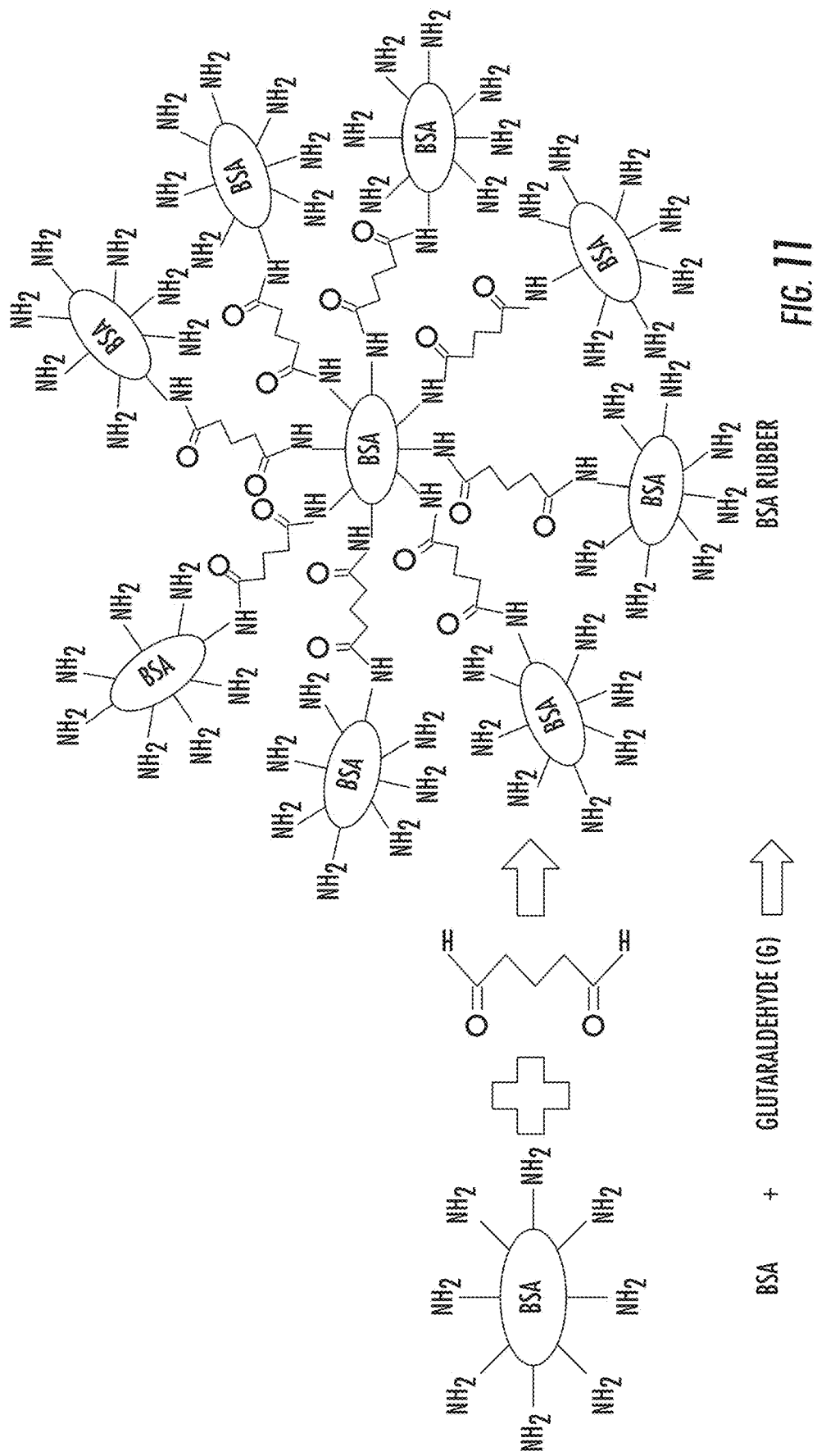
FIG. 11 shows the BSA rubber crosslinking reaction with glutaraldehyde, such that glutaraldehyde crosslinks the BSA by creating covalent bonds.

FIG. 11 depicts an exemplary BSA rubber crosslinking reaction with glutaraldehyde, such that glutaraldehyde crosslinks the BSA by creating covalent bonds. The crosslinked albumin rubber is a newly developed material, in which bovine serum albumin is crosslinked with glutaraldehyde. In most embodiments, the albumin concentration of the rubber is about 10% to about 40%, by weight of the BSA rubber (based on the wet weight). If the albumin concentration is lower than 10% by weight, the rubber becomes too soft. Conversely, if the albumin concentration is higher than 40% by weight, the rubber becomes difficult to get into solution. The glutaraldehyde concentration of the rubber is about 0.20% to about 10%, by weight (based on the dry weight of the rubber). At lower glutaraldehyde concentrations, the material does not sufficiently crosslink, the material becomes brittle at higher glutaraldehyde concentrations.

Different combinations of BSA and Glutaraldehyde concentrations in different solvents can be utilized. The rubber can be reaction injection molded into the intricate geometries of the tissue molds. Crosslinked BSA is trypsin labile and readily digested by the enzyme at mild pH and temperature conditions. Conversely, intact type I collagen is very resistant to trypsin digestion. Thus, these features allow for the selective removal of the BSA rubber leaving the collagen behind.

Other crosslinkers could include UV radiation or any multifunctional molecule targeting primary amines, carboxyls, sulfhydryls, or carbonyl groups on the proteins.

The present work focused on determination of the ideal parameters to obtain a labile mold that can deliver specific architectural features to a biocompatible scaffold. The characteristically features that were evaluated are mixability, enzyme digestion, load bearing, and ability to be reaction injected into a negative mold. It was determined that the combination of 30% BSA and 3% Glutaraldehyde fulfills these requirements. Our prototype consisted of a collagen scaffold that consists of a branched architecture. This technology provides a viable technique to deliver specific geometrical instructive to a biodegradable material which can tuned to mimic the in vivo tissue elasticity and other characteristic of the tissue of interest.

III. Fabrication of Collagen Scaffold Creation and Characterization of 3D Collagen Construct.

The BSA rubber molds can then be coated with type I collagen to create a collagen scaffold. Our novel collagen hydrogels include laminin as a cell signaling molecule.

Two distinct methods of applying the collagen can be utilized: first, a collagen dispersion can be cast around the BSA rubber mold, and second, collagen fibers can be electrospun around the BSA rubber mold. No matter the method of application of the collagen, the BSA rubber can be selectively enzyme digested away to create the inner flow paths and channels of the remaining collagen scaffold.

Electrospinning is considered to be among the most successful fabrication techniques for producing fibrous materials. Over the past decade, this technique has received growing attention due to its ability to create scaffolds that closely resemble the native extracellular matrix. Nanometer scale materials are crucial in biological systems to provide functional interactions between the molecules inside and outside of cells. In the electrospinning process a polymeric solution is placed on a syringe. The tip of the syringe is connected to a voltage source, and the collector is grounded to allow the collection of charged polymer. With no voltage, the polymer will be dispensed as droplets or as a single strand. As the polymer is subjected to the electric field, the repulsion forces act opposite to the surface tension. As the intensity of the field increases, the solution at the tip of the tube elongates, forming a conical shape known as a Taylor cone. At this point in the process, the droplet is held by its surface tension. When the electrostatic forces overcome the surface tension, a polymer solution emerges from the Taylor cone as a jet. As the jet accelerates, the solvent evaporates and thins in the electrical field. Radial charge repulsions result in an instability region on which it seems as if there is a splitting of the primary jet into multiple filaments or spraying, but the process actually creates a very fast whipping jet. To create the ideal fiber dimensions several operational parameters must be controlled such as the polymer solution (viscosity, solvent, and concentration), the electrical field, the needle dimensions, and the feed rate. There are a wide variety of electrospun materials that includes natural proteins, synthetic peptides, and blends with synthetic organic polymers.

Suitable solvents for electrospinning include fluoroalcohols, such as 1,1,1,3,3,3 hexanofluoro-2-propanol (HFP). These solvents cause conformational changes to the native structure of collagen. HFP is a highly fluorinated alcohol that destabilizes the native triple helical structure of the protein and promotes alpha helix formation. These fibers contain low denaturation temperatures similar to gelatin and can lose up to 99% of the triple helical structure. Researchers have found that approximately 45% of proline helical content of collagen is denatured using this solvent.

In one particular embodiment, native undenatured collagen fibers can be electrospun using benign acidic solvents and reaction electrospinning allowing the collagen to undergo fibrillogenesis during the electrospinning process. Using benign acidic solvents (e.g., such as water and ethanol) at low pH (e.g., about 2 to about 4 using a strong acid, such as HCl), the surface tension can be reduced sufficiently to allow for electrospinning without damaging the protein structure.

For example, the collagen can be acidified by adding a strong acid (e.g., HCl) to reduce the pH (e.g., to a pH of about 2 to about 4). Then, the collagen within the strong acid can be diluted using water and the alcohol (e.g., an alkyl alcohol such as ethanol, propanol, isopropanol, butanol, etc.), while keeping the pH relatively low (e.g., a pH of about 2 to about 5, such as about 2 to about 4). The mixture of the water and alcohol can be at a ratio of about 0.5:2 to about 2:0.5 water:alcohol (e.g., about a 1:1 ratio). This process can reversibly denature the collagen.

Then, the acidic collagen solution can be electrospun within an alkaline atmosphere. The alkaline atmosphere can serve to neutralize the acid mixed with the collagen. In response, the electrospun collagen forms collagen fibers which can be collected within a salt bath. In one embodiment the salt bath is grounded, has a pH of about 7.5 to about 9, and/or includes ammonium sulfate in water.

IV. Fabrication of a Branched Vascular Tissue and/or Cell Culture

Vascular tissue constructs can then be created using two cells types, vascular endothelial cells (VECs) and pluripotent bone marrow stromal cells (BMSCs). The construct made with VECs can be assayed for formation of a functional endothelium; whereas, the construct made with BMSCs can be assayed for the vascular tissue formation.

EXAMPLES

In these Examples, PBS refers to a phosphate buffered saline, with a composition of:

| Chemical | Concentration (mmol) |
|---|---|
| NaCl | 137 |
| KCl | 2.7 |
| $Na_2PO_4$ | 10 |
| $KH_2PO_4$ | 1.8 |

Example A

Example 1.1: Image the Internal Flow Path of Developing Hearts

Figure 2A:
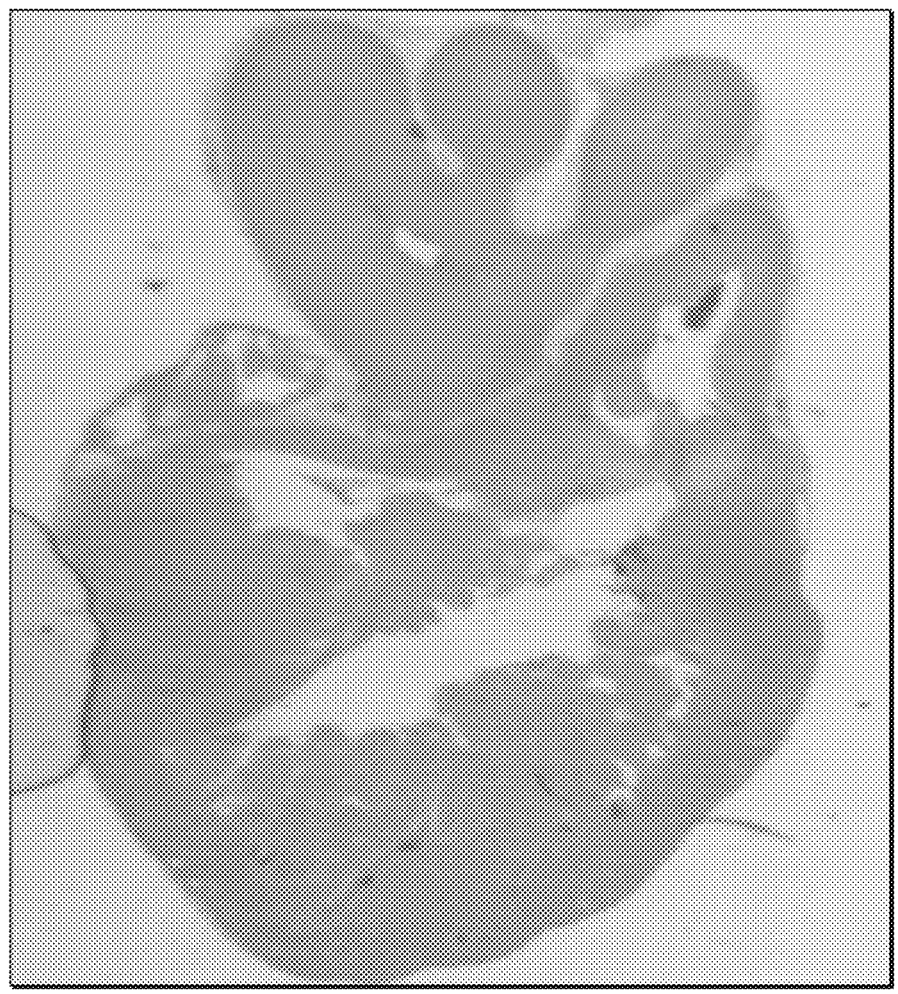
FIG. 2a shows Mastercam Art using a cross sectional heart slice at stage 40.

Native, in vivo, flow channels have geometric features specific to the function of the tissue. Using high resolution microscopy, these features can be captured and measures in a series of 2D images. Amira® software is a powerful tool that has been used to recreate specific 3D architecture from 2D images (Smarr, Wirrig, Phelps, Trusk, & Wessels, 2007). Amira® was used to determine the precise dimensions of the pulmonary trunk and the right ventricle of a chick heart and to create 3D models of the heart at different stages (FIG. 1). FIG. 2(a) shows an image of one of the several cross sectional areas of the heart that was imported to create the 3D model in FIG. 1.

Tissues can be isolated and fixed in 4% paraformaldehyde. The fixed tissues can be embedded and sectioned at 8 μm. Confocal or light microscopy can then be used to obtain detail images with the intrinsic geometrical features. For light microscopy, the sections can be stained with hematoxylin (nuclei) and Eosin (cytoplasm, collagen, and muscle fiber). For confocal microscopy, several antibodies can be used such as Dapi (nuclei), phalloidin (cytoskeleton), α-SMA (smooth muscle actin), PECAM (endothelial), among others. Using Amira®, these images can then be assembled into 3D model reconstitutions. This model is then imported to Mastercam Art®, where it is converted into a G code and further machined it using the Microlution®363-S. This fabricated piece upholds the precise dimensions for a variety of tissues.

Figure 2B:
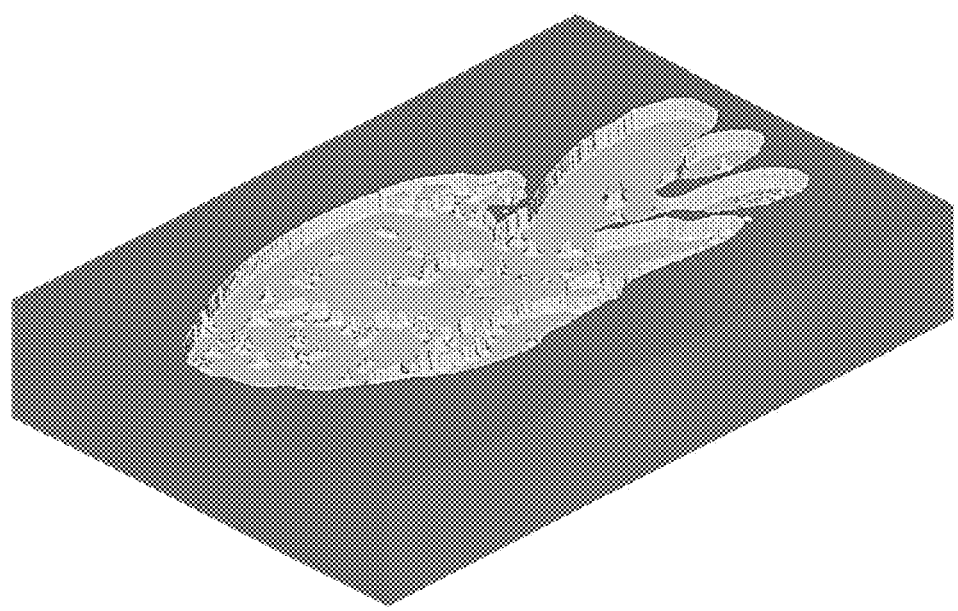
FIG. 2b shows the replicate of the image of FIG. 2a after it was imported into Mastercam Art to replicate the precise complex dimensions.

FIGS. 2a and 2b are an example of how a solid can be generated in Matercam Art by importing a single image of a cross-sectional area of a chick heart obtained from Light Microscopy. The generated solid mimics the in vivo architecture of the tissue.

Figure 3A:
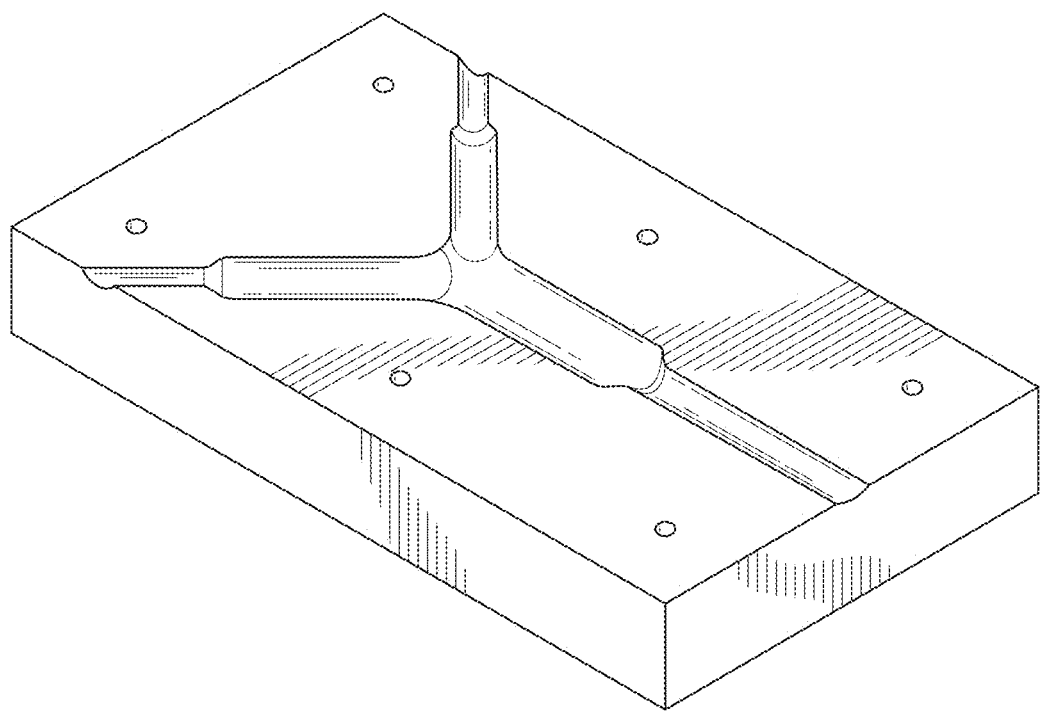
FIG. 3a shows a Mastercam 3D representation of a branch vasculature where the far left tracts have different dimensions (lower diameter=3 mm, upper diameter=2 mm).
Figure 3B:
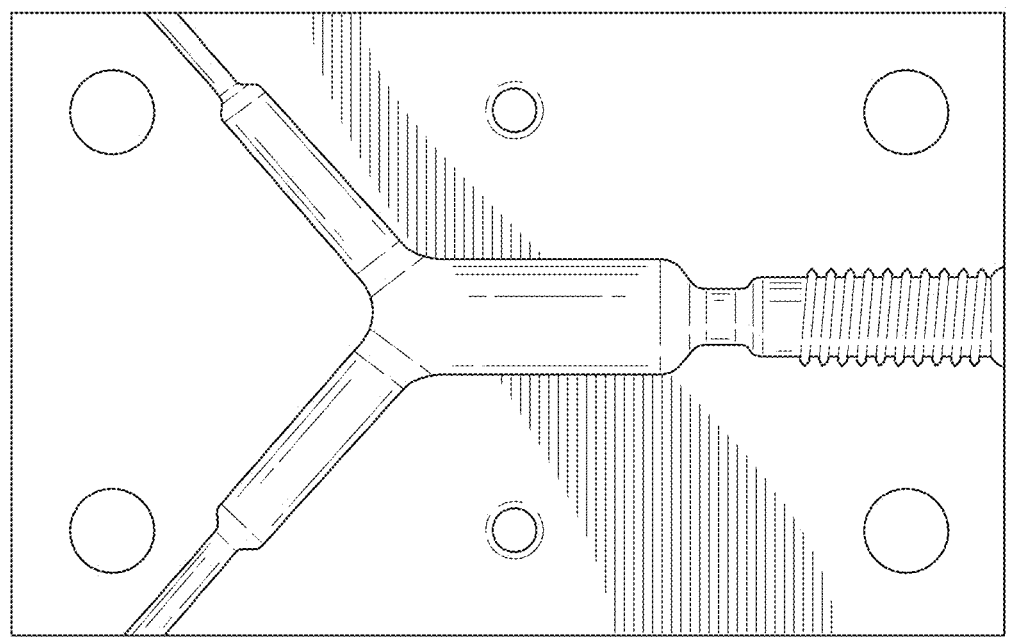
FIG. 3b shows a stainless steel mold created with the same dimensions of FIG. 3a using the Microlution Machine.

Alternately, the in vivo geometries of the tissue voids in a mold piece can be obtained by constructing a solid in Mastercam®. FIGS. 3a and 3b show the solid created in Mastercam® in which precise dimensions were created on each of the branches.

Example 1.2: Image the Internal Flow Path of the Renal Artery from the Hilus to the $3^{rd}$ Branch Point Kidney transplantation is now a routine surgical procedure with a success rate of 90-95% one year after implantation. However, shortage of organ donors creates a waiting list of 60,000 patients, many of whom die before a suitable donor kidney is found. Although modern dialysis (artificial kidney) saves human lives, it is not a radical but rather a palliative, temporal and very expensive solution that costs an average of $250,000 to maintain the life of one patient with end stage kidney disease. Kidney diseases consume 6% of Medicare expenditures in the US. One of the critical features of creating an engineered tissue such as the kidney is the multiple branching architecture of the renal artery.

The kidney can be dissected from 300 gram previously sacrificed male Sprague Dawley rats. The renal arteries can be sectioned and imaged from these animals as described above. These images will be used for 3D reconstruction as described.

Example 2: Bovine Serum Albumin Rubber Fabrication and Subsequent Selective Enzyme Digestion The BSA rubber was prepared using bovine serum albumin crosslinked with glutaraldehyde. The rubber can be reaction injection molded into the intricate geometries of the tissue molds created in Examples 1 and 2.

Figure 4B:
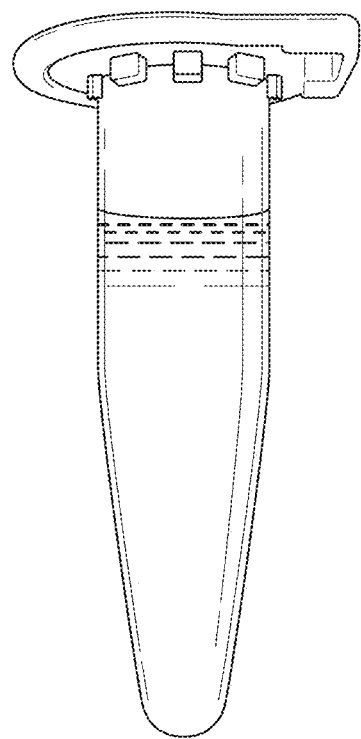
FIG. 4b shows BSA rubber digested by Trypsin solution according the Examples.
Figure 4C:
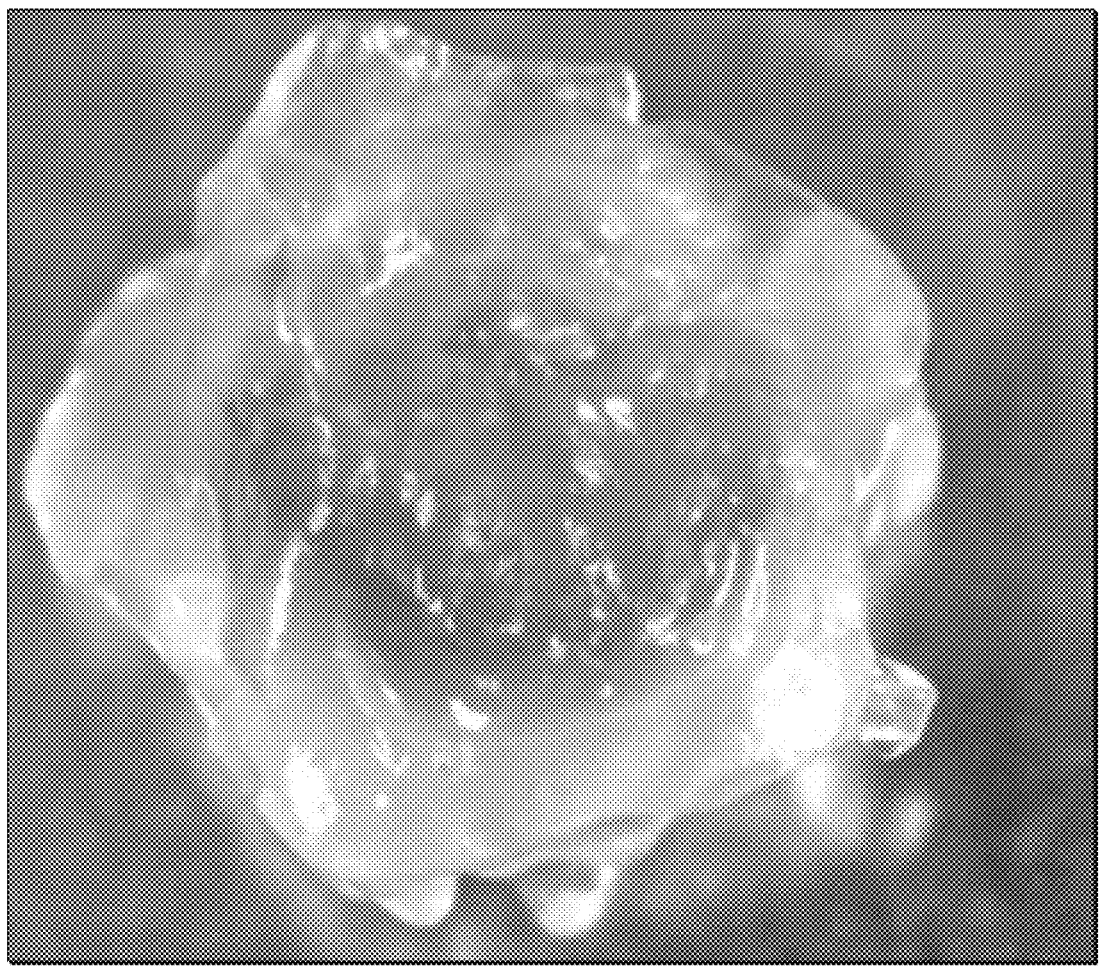
FIG. 4c shows BSA rubber punch cover with collagen prior to polymerize according the Examples.
Figure 4D:
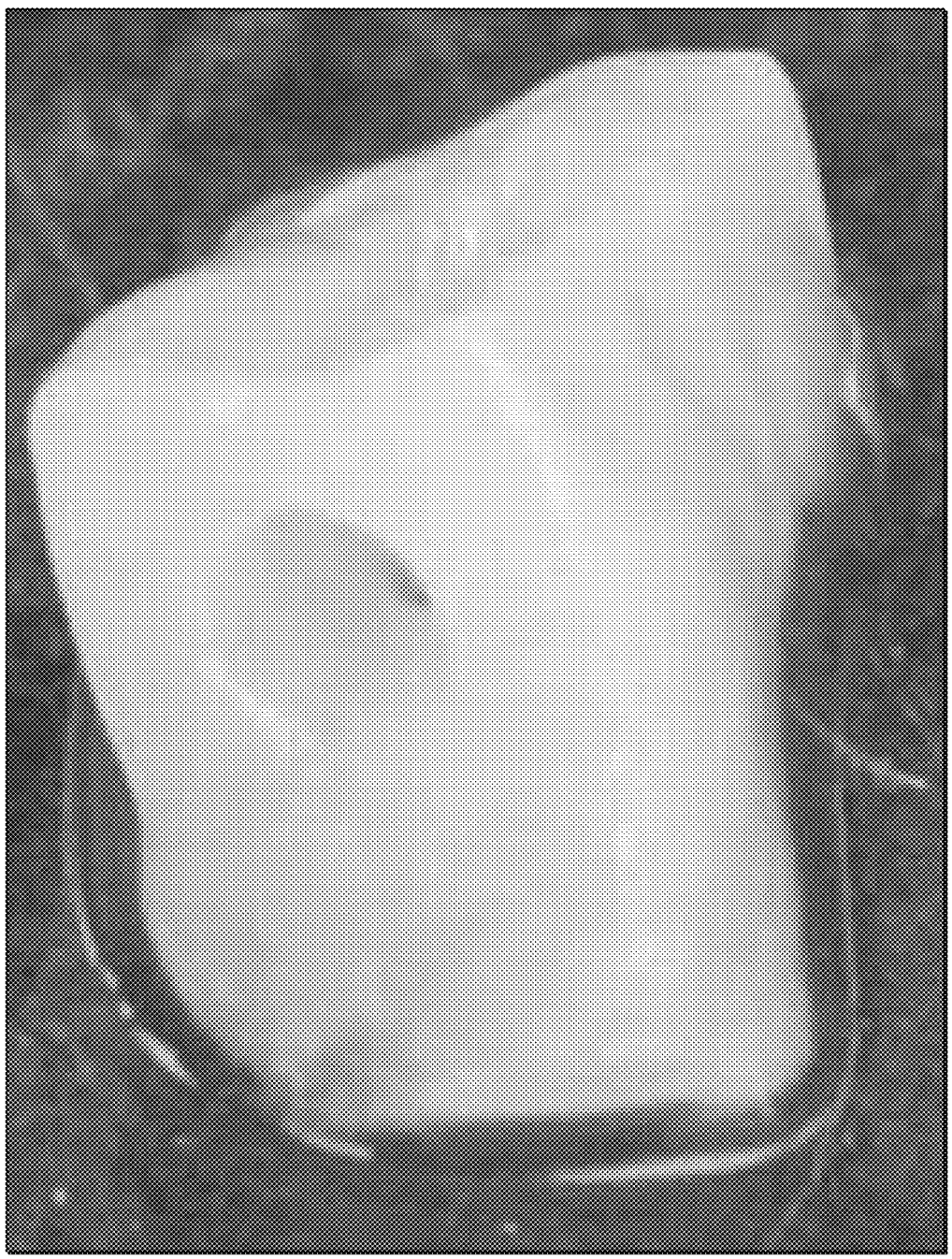
FIG. 4d shows collagen hydrogel with a 4 mm diameter channel according the examples.
Figure 5:
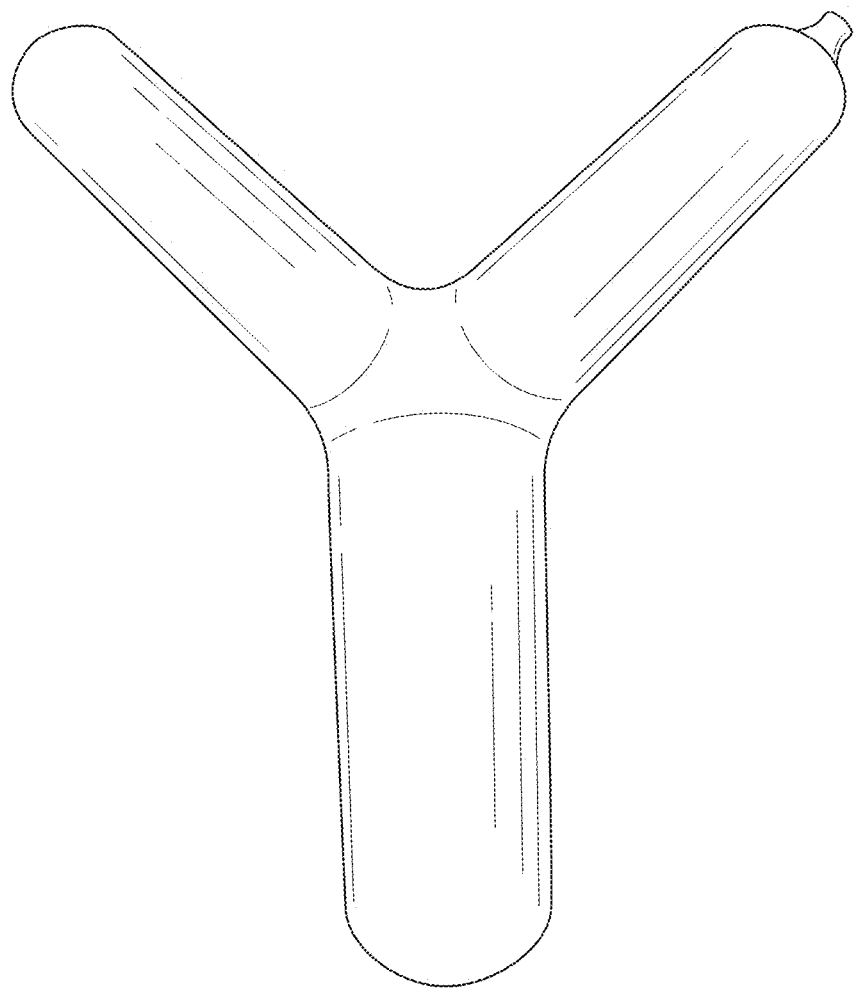
FIG. 5 shows a "Y" BSA rubber made using the mold created previously in FIG. 3b. The BSA and the Glutaraldehyde were reaction injected into the mold where it had a reaction time of approximately 24 hr, according to the Examples.

The BSA rubber can then be enzyme digested as seen in FIG. 4b using trypsin at the proper pH and temperature. Preliminary data suggests that at pH 7.8 and temperature of 30° C. for 15 hr, the BSA rubber can be digested with minimal impact on the collagen scaffold. FIG. 4d shows a 4 mm diameter channel inside a collagen hydrogel after enzyme digestion of the BSA rubber.

Figure 6:
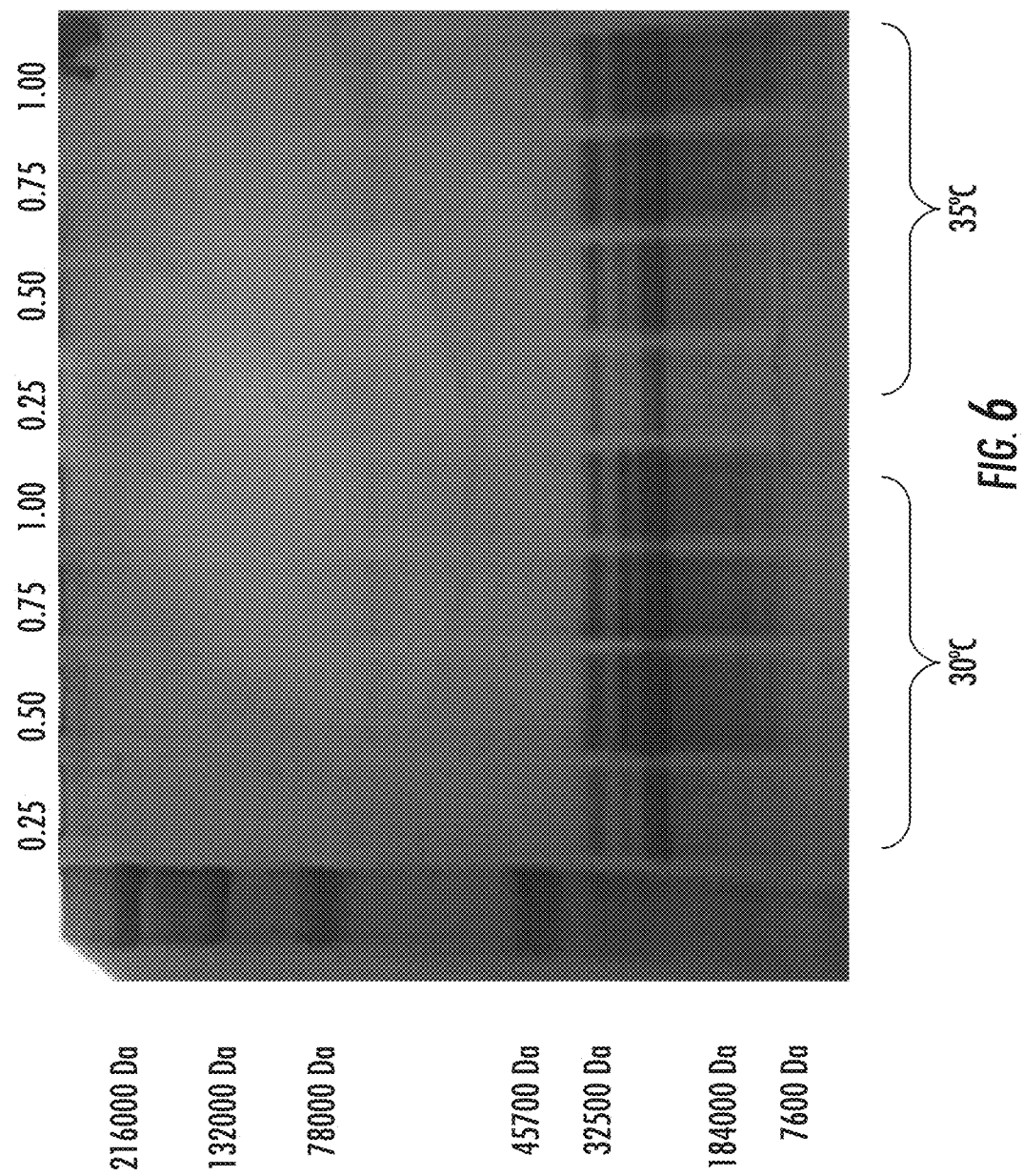
FIG. 6 shows the Typsin Concentration through Coomassie staining of the supernatant followed by trypsin digestion: The collagen hydrogel containing the BSA rubber was placed in contact with several trypsin concentrations (0.25%, 0.5%, 0.75%, and 1%), pH conditions (5.5 or 7.8), temperatures (30° C. and 35° C.), and at different time points (0, 24, 48, and 72 hr). The above figure shows the spread in molecular weights after a 72 hr period in the presence of trypsin with a pH of 5.5. At 48 hr there is some collagen in the form of collagen hydrolase which showed at 50 KDa. These bands disappear at the 72 hr time point, indicating their degradation. Lowry assay was used to quantify the total protein in trypsin solution was quantified prior and after the collagen-BSA rubber were place in contact using.

Coomassie® (Imperial Chemical Industries) staining of PAGE gels on supernatant after enzyme removal of BSA rubber shows little collagen or collagen fragments in solution (FIG. 6). A Lowry assay was performed to quantify the total protein content in solution (Tables 1 and 2 below). Specifically, the amount of protein of the collagen and BSA rubber placed in the different enzyme concentration and conditions was quantified (temperature, time points, and pH). At 72 hr, there is a decrease in the amount of protein, indicating their degradation into amino acids.

TABLE 1

Total protein concentration (μg/mL) at 30° C. and pH 7.8

| Trypsin concentration (%) | Time (hr) | | | |
|---|---|---|---|---|
| | 0 | 24 | 48 | 72 |
| 0.25 | 152.476 | 182.091 | 334.086 | 145.202 |
| 0.50 | 283.910 | 370.960 | 533.972 | 263.949 |
| 0.75 | 476.239 | 596.041 | 458.797 | 150.203 |
| 1 | 446.281 | 465.141 | 505.283 | 414.085 |

TABLE 2

Total protein concentration (μg/mL) at 35° C. and pH 7.8

| Trypsin concentration (%) | Time (hr) | | | |
|---|---|---|---|---|
| | 0 | 24 | 48 | 72 |
| 0.25 | 152.476 | 280.265 | 361.766 | 165.433 |
| 0.50 | 283.910 | 502.116 | 414.040 | 424.037 |
| 0.75 | 476.239 | 633.442 | 932.943 | 590.006 |
| 1 | 446.281 | 652.142 | 1565.139 | 677.967 |

Using these techniques, the appropriate conditions to remove the rubber and maintain the integrity of the collagen hydrogel can be determined.

Example 3.1: Collagen Scaffold Creation and Characterization

Our BSA rubber molds can be coated with type I collagen to demonstrate the fabrication methods and technology, using two distinct methods of applying the collagen: first we will cast collagen dispersion around the BSA rubber mold and second we will reaction electrospin collagen fibers around the BSA rubber. In each case, the BSA rubber will be selectively enzyme digested away to create the inner flow paths and channels of the scaffold.

In this example, the novel fabrication process in which the BSA rubber is covered in collagen fibrils and the rubber selectively enzyme digested away leaving the intricate flow channels behind.

Example 3.2: Create the Collagen Scaffold by Casting

Casting is a well-recognized, simple fabrication technique that yields quality products. The original formula for the cell instructive collagen hydrogels is casting of the gels. We have characterized the cast gels using shear rheometry.

The hydrogels will be created using specific collagen concentrations and 10 ug/mL of laminin. Both of these components are natural constituents of the extracellular matrix. Laminin was selected to promote cell adhesion and, in the endothelial cells, induce its tubular formation (Madri, Patt, & Tucker, 1988). To polymerize the collagen, MEM and HEPES were added in an 8:1:1 ratio at 4° C. The gels were casted and placed in 37° C. incubator for 1 hr. After the incubation period, the hydrogels were UV crosslinked using an energy source of 630000 microjoules per centimeter squared.

Experiments in this example will focus on obtaining an integral collagen hydrogel that mimics the in vivo geometrical features in an economical and simple process. We will use the above techniques to cast collagen hydrogels on various BSA rubber geometries and characterize these scaffolds in aim 3 sub aim 3.

Example 3.3: Create the Collagen Scaffold by Reaction Electrospinning of Collagen Gel Dispersion Reaction electrospinning is a new technique we have developed in our laboratory. It allows us to make collagen scaffolds with varying fiber diameters and varying size of voids and openness of the woven structure. Reaction electrospun collagen is different from solvent based electrospun collagen. In reaction electrospinning, swollen dissociated collagen monomers and microfibrils are formed into thin fibers by the electric field, spun into an anhydrous ammonia atmosphere and into a solution of ammonium sulfate. The fibrils undergo fibrillogenesis and reprecipitate native banded collagen fibrils within the spun fibers. Solvent based electrospun collagen is essentially solvent denatured collagen that does not undergo fibrillogenesis and restore its native architecture. Also, solvent electrospun collagen must be chemically crosslinked to retain its integrity. Typically, these chemical crosslinkers such as glutaraldehyde are cytotoxic. Commonly used solvents are fluoroalchols, which has been shown to degrade the collagen, creating gelatin scaffolds (Zeugolis, et al., 2008).

Figure 7:
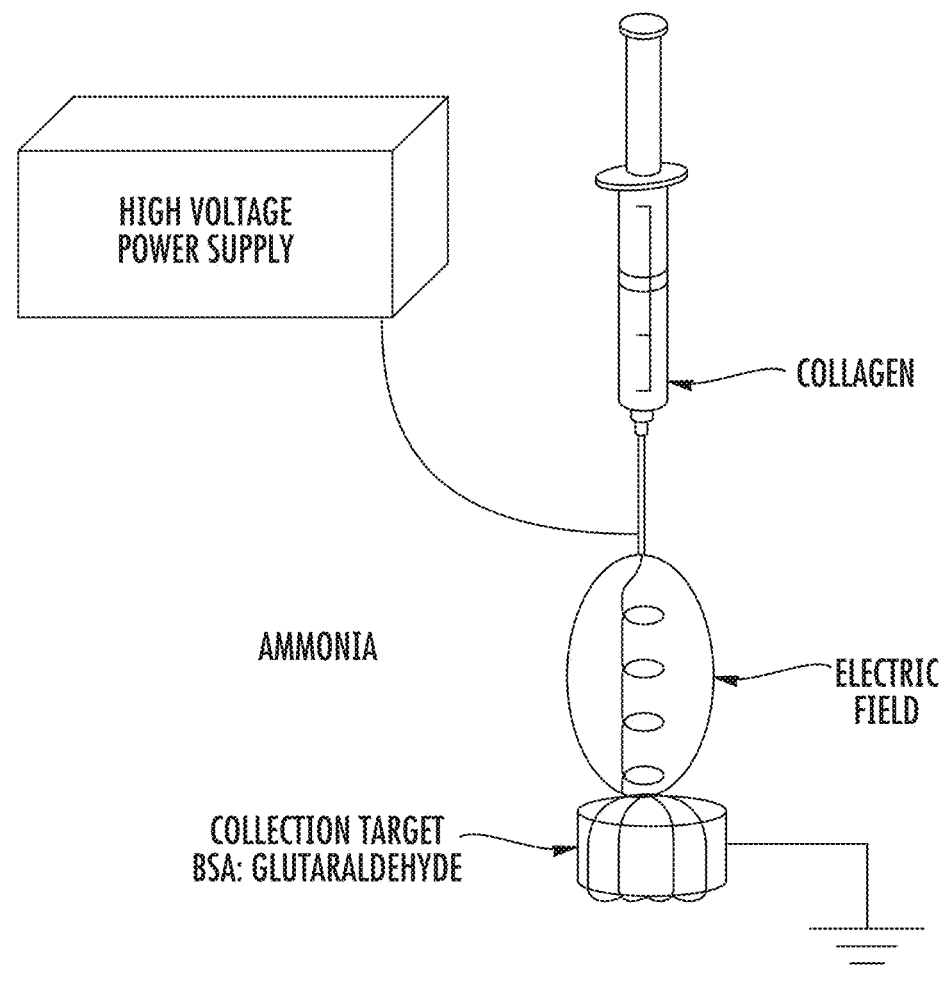

Using our current electrospinning setup showed on FIG. 7, we have used several concentrations of acidified collagen and obtained reaction electrospun collagen hydrogels. We, along with other have included ethanol in the dispersion to overcome the high surface tension of water that contributes to poor electrospinning of water based polymers (Dong, Arnoult, Smith, & Whek, 2009). Our initial parameters consists of using 1-4% collagen concentrations, ethanol: water ratios from 1:1 to 2.3:1, 15 KV of voltage, an air gap of 2-6 cm, and a flow rate of 1 mL/min. The dispersion recipes at 1-2% collagen concentration yield hydrogels with a final Young's modulus of 1 to 19 kPa. The literature, and our own work, has shown that this range is particularly effective at modulating cell phenotype and differentiation (Gilbert, et al., 2010). Therefore, experiments in this sub aim will focus on statistical experimental design (D-optimal initially followed by response surface) of the electrospinning parameters of anhydrous ammonia gas gap, electrical field strength, dispersion feed rate, final spinneret tip length, and final spinneret tip diameter. The measured parameters are collagen fiber diameter, spun fiber length and total spun scaffold yield. Materials prepared in this sub aim will be further characterized in aim 3 sub aim 3 where we will measure the Young's modulus of the finished material and further characteristics as described. Analysis will be by ANOVA followed by 2 way interaction linear statistical modeling.

Example 3.4: Characterize the Collagen Hydrogels Using Shear Rheometry, Scanning Electron Microscopy, Biochemical Analysis and Minimal Stable Dimensional Analysis In our preliminary data we have demonstrated how we can characterize the bulk viscoelastic properties of our collagen hydrogels using the shear rheometer. Recent reports in the literature suggest that the bulk properties of hydrogels are cell instructive (Gilbert, et al., 2010). The concentration and distribution of cell receptor sites is cell instructive (Lutolf & Hubbell, 2005; Yost, et al., 2004; Simpson, Terracio, Terracio, Price, C, & Borg, 1994) which is characterized biochemically and immunohistochemically. Our own data has shown that collagen fibril organization is in cell instructive and directs cell phenotype (Yost, et al., 2004). This is best characterized using Scanning electron microscopy (SEM).

Figure 8A:
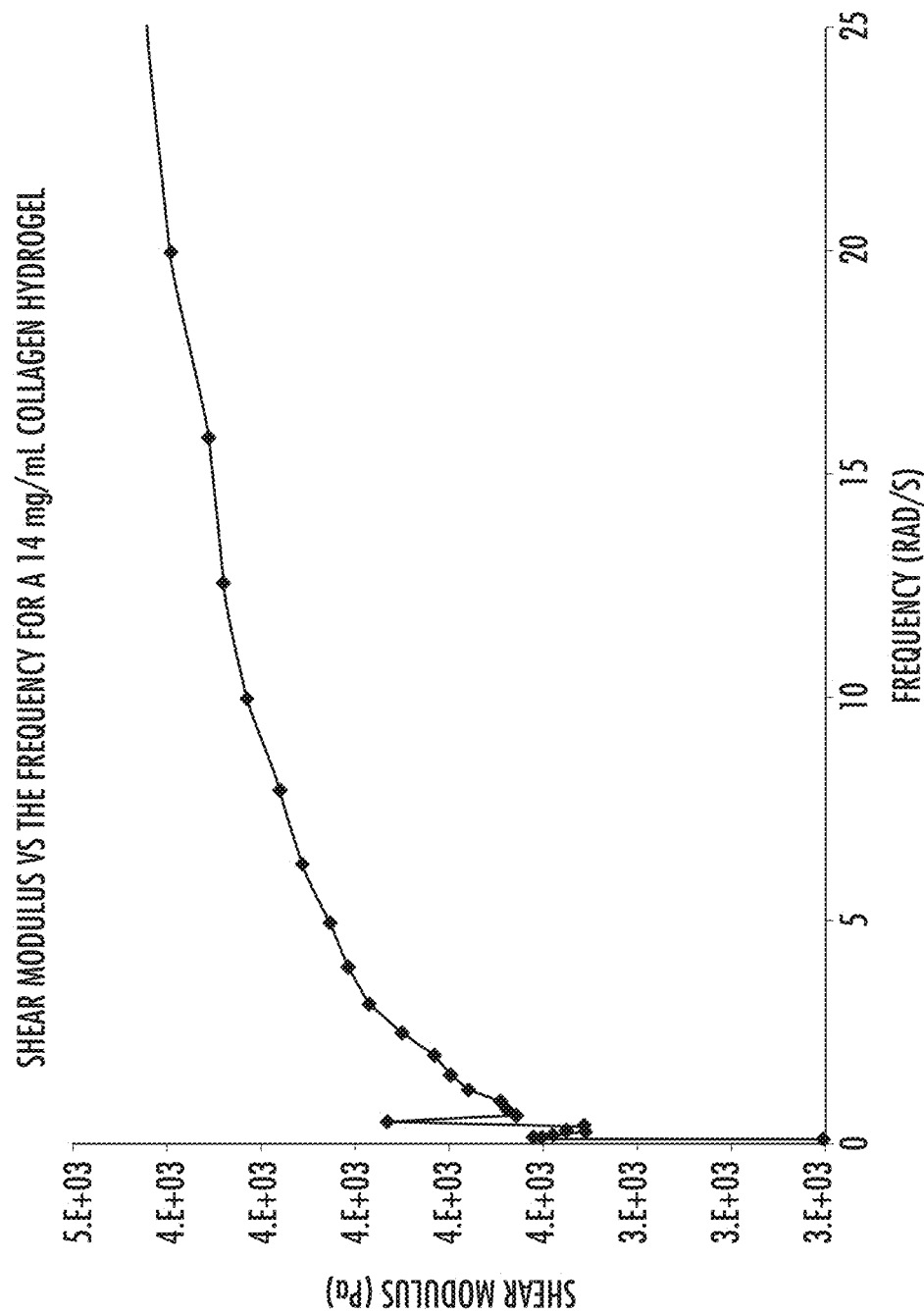
FIG. 8a shows the shear modulus response on a frequency range of 0.2-4.3 Hz on a sample using the RFSII to measure the hydrogel's shear modulus. The sample was loaded between the parallel plates.
Figure 8B:
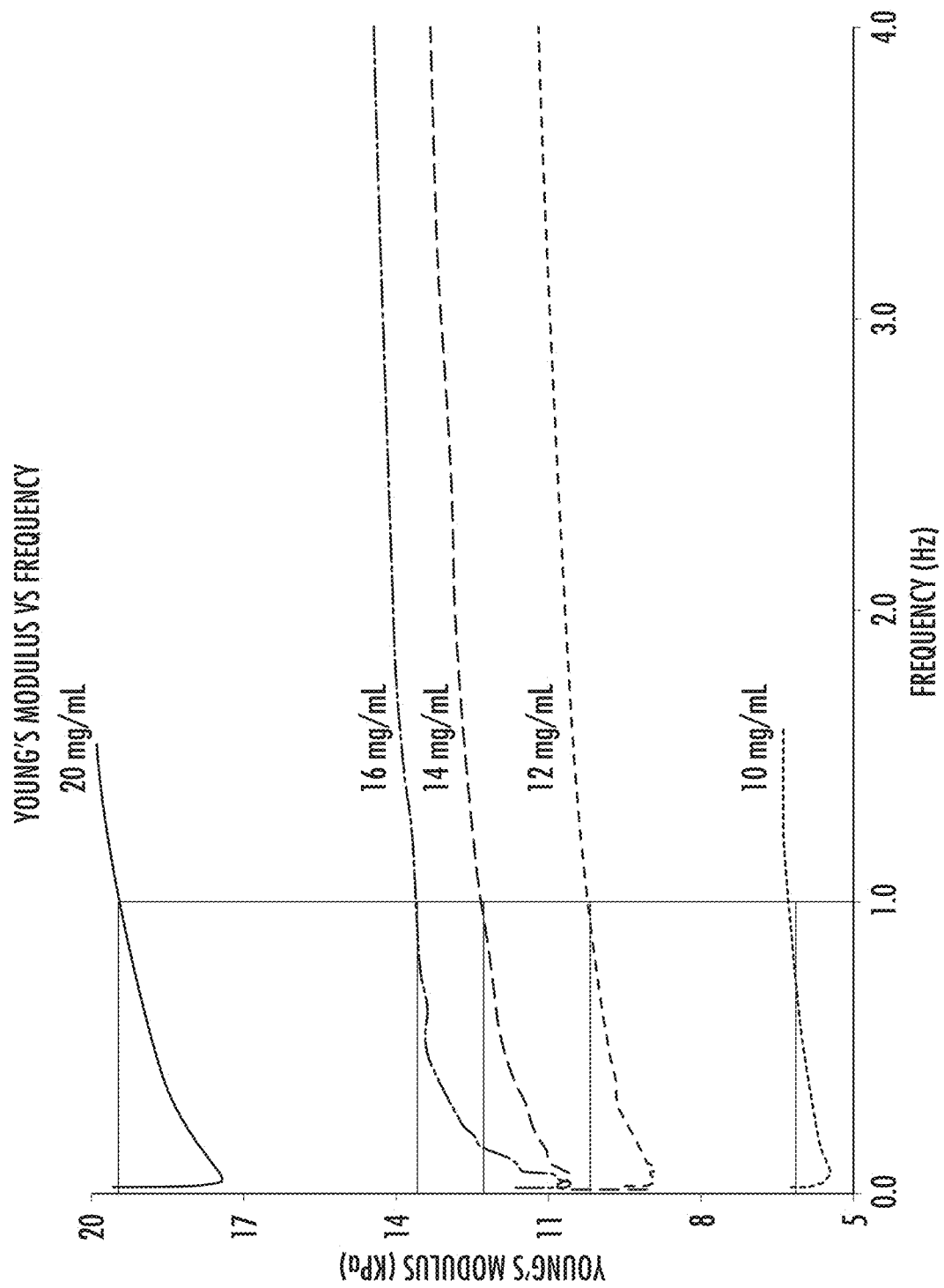
FIG. 8b shows the elastic modulus response to frequency for varying concentrations of collagen.
Figure 8C:
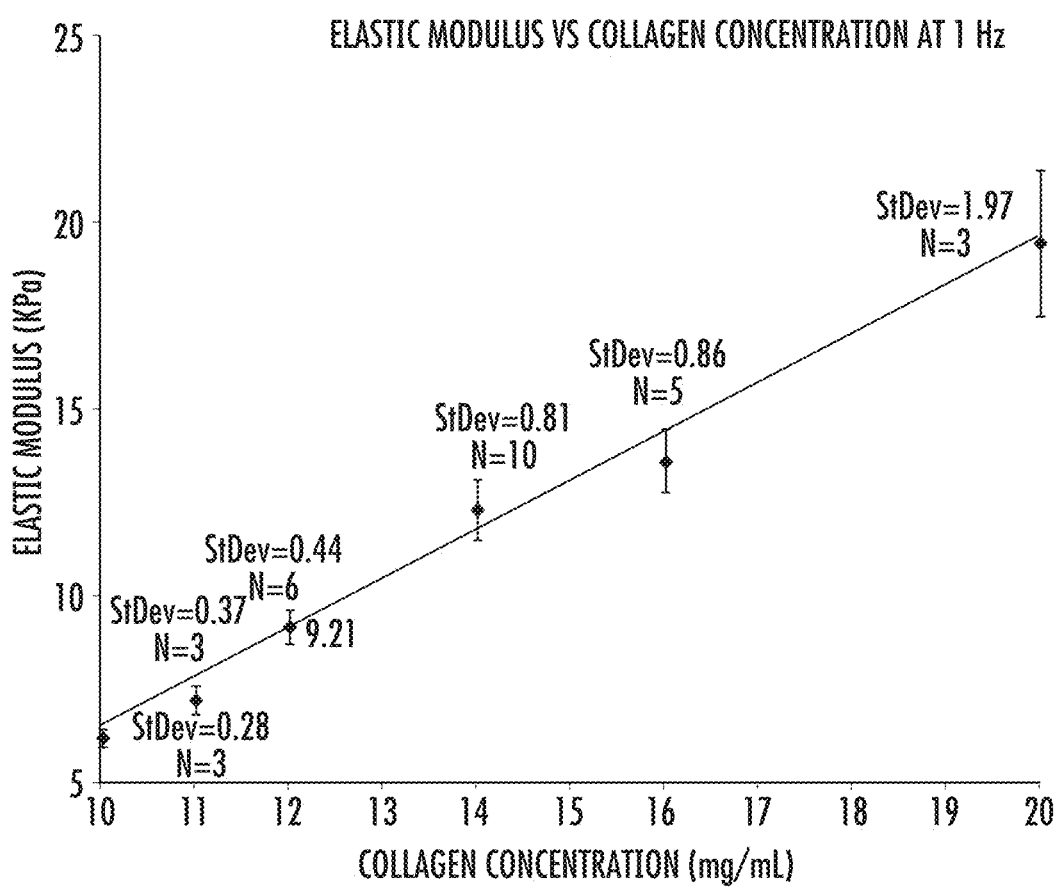
FIG. 8c shows a linear regression fit of the elastic modulus versus collagen concentration collected at 1 Hz; the error bars represent+/− standard deviation.

Collagen hydrogels with a concentration of 10 to 20 mg/mL were placed on the parallel plates assembly of the Rheometrics Fluid Spectrometer RFS II, which was used to obtain the shear modulus for each of the samples. Since these hydrogels are designed to be used in cell culture and in vivo transplant, the measurements were conducted in isothermal conditions at 37° C. The shear modulus (G') was recorded at constant strain (0.5%) as a function of frequency (0.10 rad/s to 25 rad/s or 0.016 Hz to 4.0 Hz) with 25 data points recorded as seen in FIG. 8a. The rheometer consists of a parallel plate assembly of 25 mm diameter that was compressed until the hydrogel exerted a normal force opposite to the assembly. The parallel plates were covered with a 120 grit sandpaper to avoid slipping of the sample. Collagen behaves as a viscoelastic material. The data points obtain at 1 Hz were reported in which constitutes the linear region of the elastic material. The material obeys Hooke's law in that the strain is directly proportional to the stress. The collagen fibers by themselves have anisotropic behavior but as a whole we assume that the collagen in the hydrogel were randomly oriented behaving as an isotropic material. These assumption was correlated using a cross polarized light microscope were we saw some birefringence of the collagen. However, birefringence did not change as the sample's orientation changed with respect to the polarized light. We converted this data to Young's modulus using the following equation: $E'=2(1+v)G'$ where $E'$ is the Young's modulus or elastic modulus, $G'$ is the storage or shear modulus, and $v$ is the Poisson's ratio. The relationship between the Young's modulus and the collagen hydrogel concentration is linear based on our concentration range, as seen on FIG. 8c. We assumed a Poisson's ratio of 0.5 because the collagen hydrogel is a perfectly incompressible material deformed elastically at very small strains.

Using the preliminary data, which relates the collagen concentration to the Young's modulus, we will determine the influence of the cell-matrix interactions and the ability of the cell to proliferate and/or differentiate. By manipulating the modulus and incorporating detail structural component of the in vivo niche, we can obtain and control specific phenotypes expression (Gilbert, et al., 2010; Yost, et al., 2004). Researchers have shown that the regenerative capabilities of certain stem cells are lost once they are grown on standard tissue culture plastic, which is stiffer than their in vivo niches, and produce progenitors with a decrease in their regenerative potential (Montarras, 2005; Gilbert, et al., 2010). The same concept applies to vasculogenesis: we need to provide the adequate environment for the formation of vasculature, providing the proper biological cues. Valarmathi et al. used bone marrow stromal cells in our 3D tubular collagen scaffold, which was able to support vasculogenic differentiation. The collagen hydrogels at different modulus will be cultured with vascular endothelial cells (VECs) and pluripotent bone marrow stromal cells (BMSCs). Using confocal microscopy we will be able to determine the phenotype expression using antibodies such as α-SMA (smooth muscle actin), PECAM (endothelial), among others.

Figure 9:
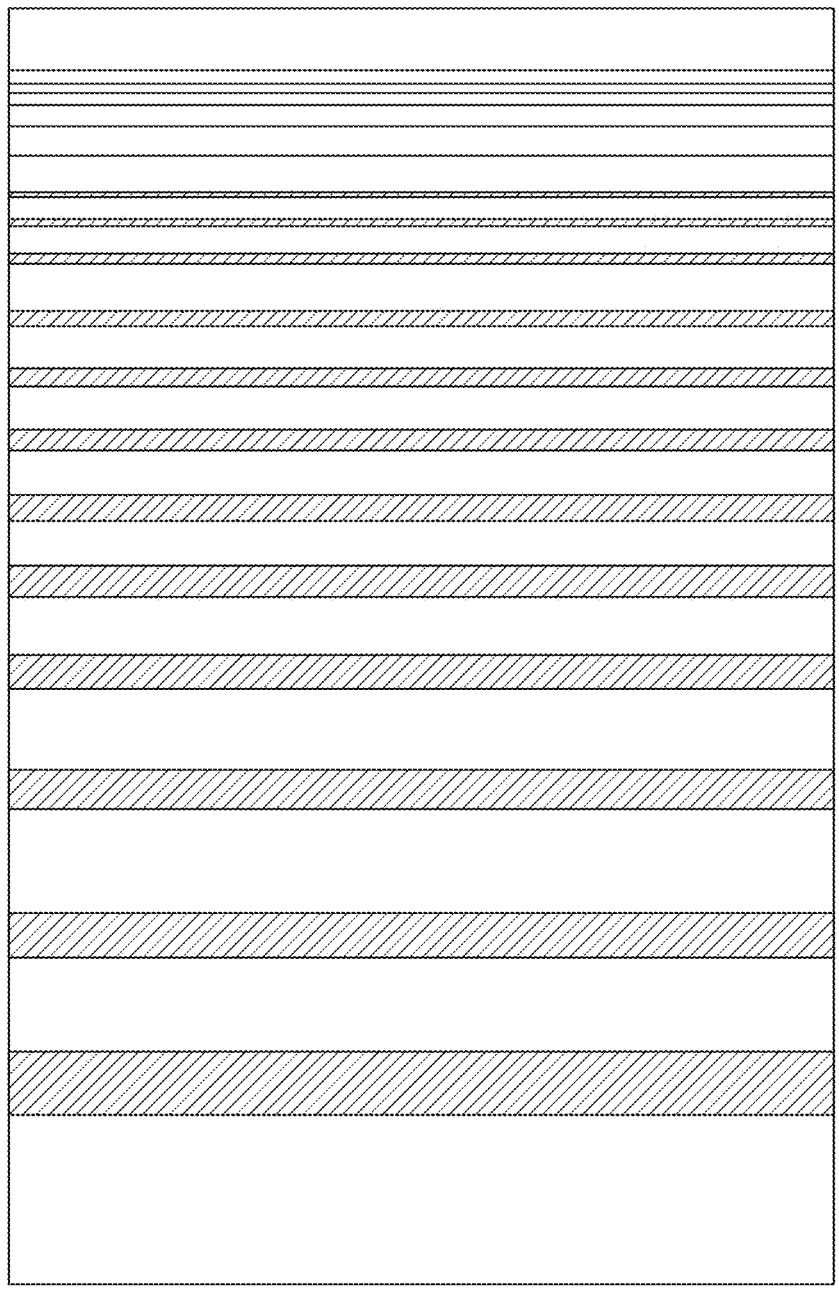
FIG. 9 shows a test blank for BSA rubber collagen scaffolds. The lines represent the grooves and the white space the lands. From left to right, the largest spacing and groove width is 5 mm each. These features diminish to 20 micron grooves with 20 micron spacing. We will coat the molds with silicone mold release and reaction injection mold the BSA rubber into these blanks under vacuum. We will then release the rubber and determine the last set of lands and grooves where we get a full mold. The BSA rubber will be further processed by collagen coating and enzyme removal. Finally, we will determine the dimensions of the smallest stable feature in our collagen scaffolds.
Figure 10A:
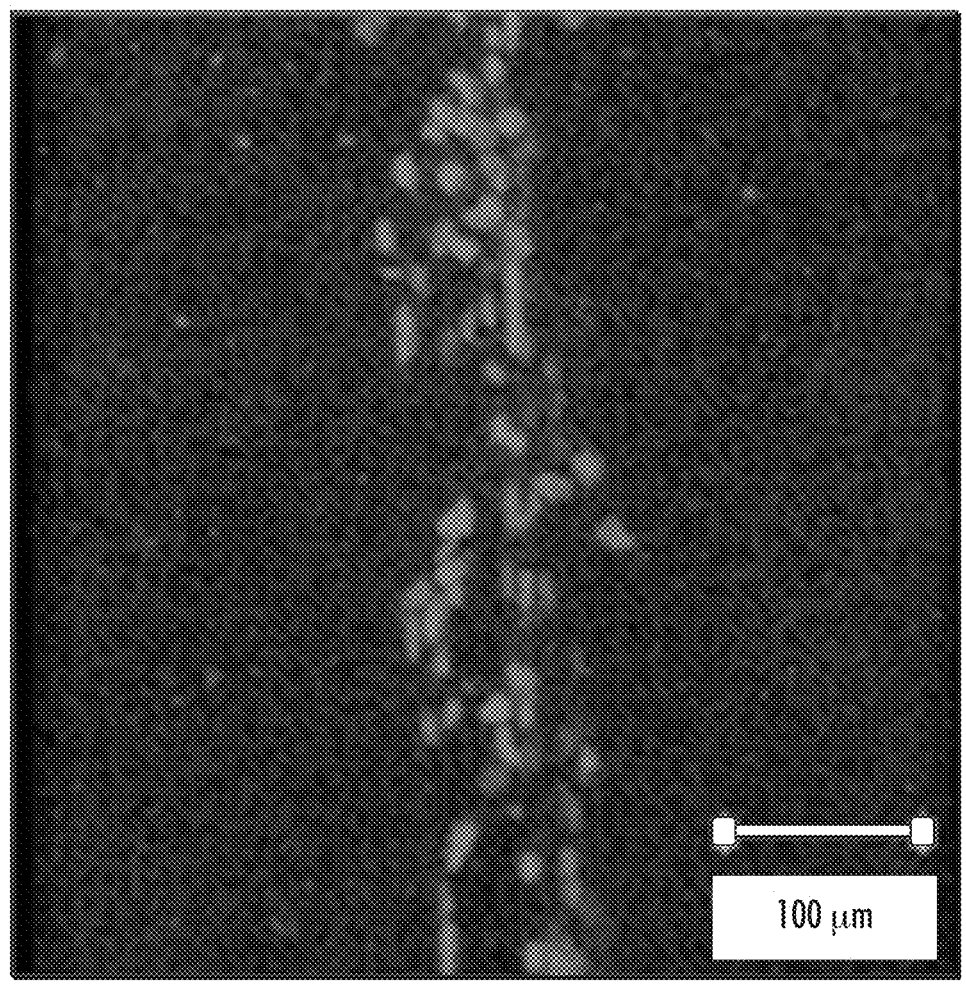
FIGS. 10a-10d show in vitro channels inside the collagen hydrogels. The channels of a 1.4% collagen hydrogel were cultured with Bone Marrow cells. After two days in culture, cells were fixed in 4% PFA solution. The hydrogel was embedded in agarose solution. Using the Vibratome, the specimen was sliced maintaining a thickness 200 um.
Figure 10B:
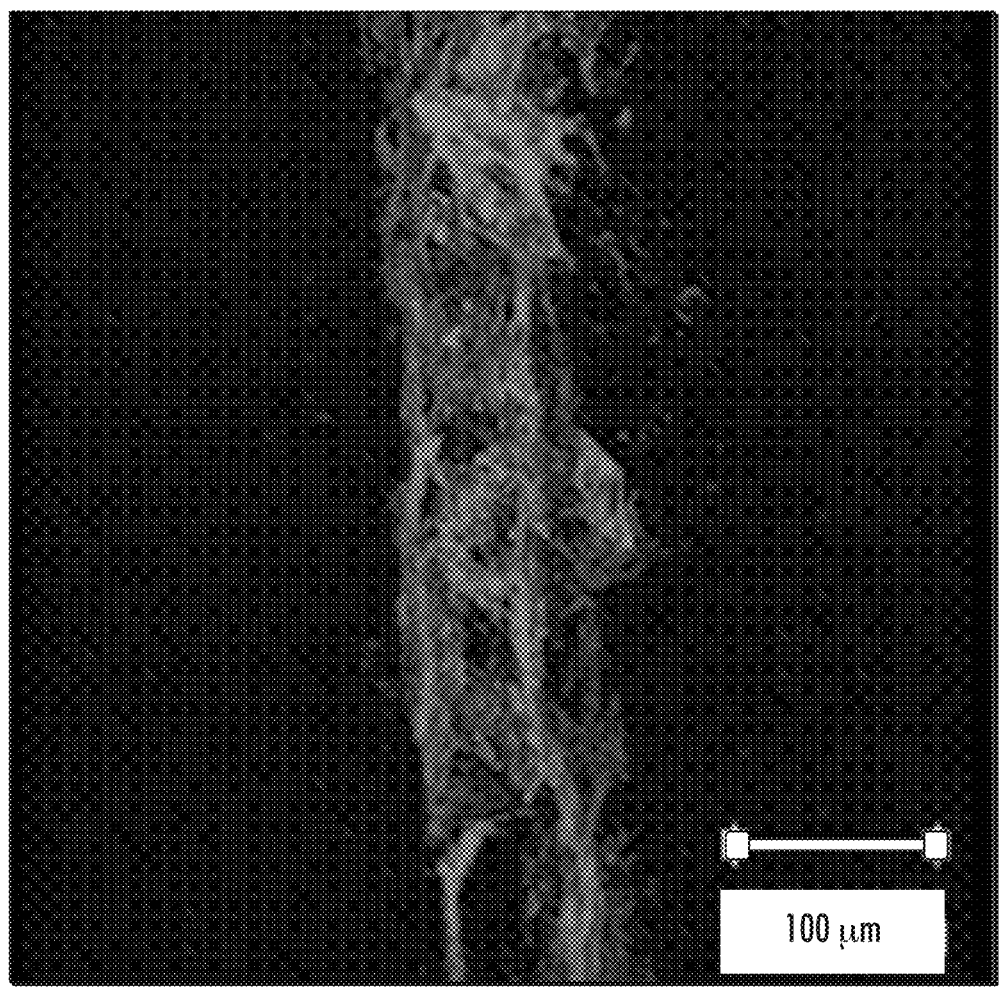
Figure 10C:
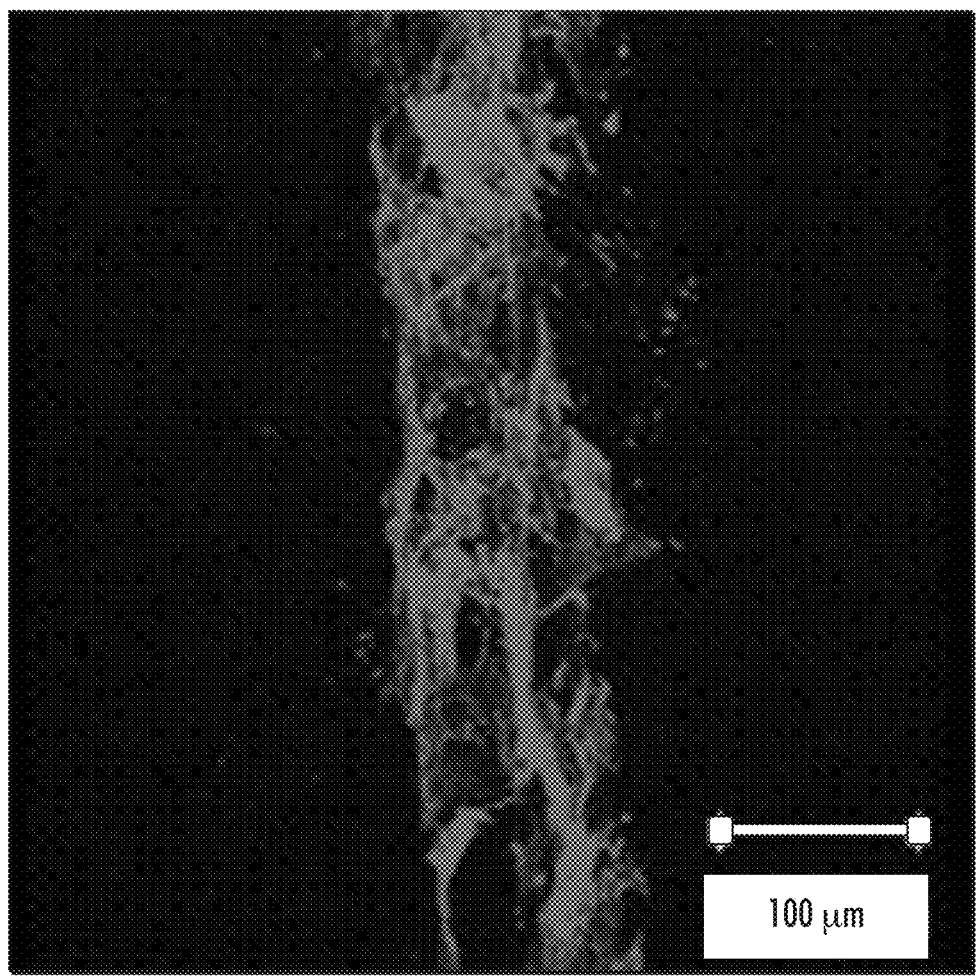
Figure 10D:
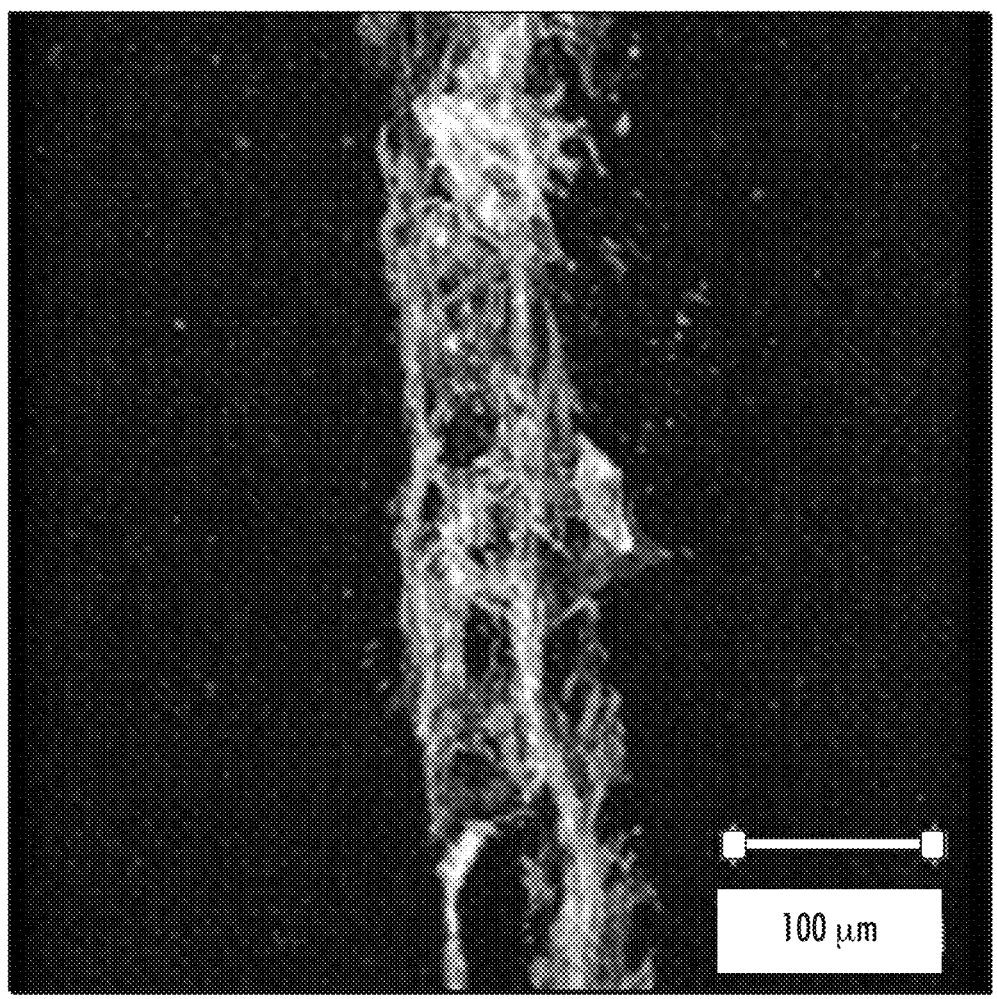

We have developed a method to characterize the minimum dimensions that are stable through our manufacturing process. The 363-s is capable of using a 2 micron cutter and accurate sub-micron positioning. However, it is uncertain how small a feature we can successfully reaction injection mold with the rubber and how stable that dimension is through the collagen coating and subsequent rubber removal. To this end, we have machine blanks of alternating lands and grooves with diminishing dimensions to test our process. FIG. 9 is a schematic of our blank and test method description.

These features diminish to 20 micron grooves with 20 micron spacing. We will coat the molds with silicone mold release and reaction injection mold the BSA rubber into these blanks under vacuum. We will then release the rubber and determine the last set of lands and grooves where we get a full mold. The BSA rubber will be further processed by collagen coating and enzyme removal. Finally, we will determine the dimensions of the smallest stable feature in our collagen scaffolds.

Example 4.1: Fabrication of a Branched Vascular Tissue, Cell Culture, and Cell Culture Characterization We will culture two cells types, vascular endothelial cells (VECs) and pluripotent bone marrow stromal cells (BMSCs). The construct made with VECs will be assayed for formation of a functional endothelium; whereas, the construct made with BMSCs will be assayed for the vascular tissue formation.

It is believed that cell behavior is regulated in part by the composition, modulus and geometric features of its specific micro-environment. Thus, we will create collagen hydrogels with mechanical properties and geometric features. These hydrogels will be seeded then with vascular endothelial cells or bone marrow stromal cells. The specific rationale for each cell type is provided below. We will measure cell behaviors such as cell phenotype, proliferation, differentiation, specific cell junction protein expression and apoptosis. A comparison of these cell parameters will provide important clues as to how the cells are responding to our novel scaffolds.

Example 4.2: Culture Endothelial Cells on Both the Cast and Reaction Electrospun Scaffolds Most hollow tissue structures are lined with endothelial cells the make up the endothelium. The endothelium is the thin layer of cells that lines the interior surface of blood vessels forming an interface between circulating blood in the lumen and the rest of the vessel wall. Endothelial cells line the entire circulatory system, from the heart to the smallest capillary. These cells reduce turbulence of the flow of blood, allowing the fluid to be pumped farther.

The endothelium normally provides a non-thrombogenic surface because it contains heparan sulfate, which acts as a cofactor for activating antithrombin III, a protease that inactivates several factors in the coagulation cascade. Their main purpose is the barrier function—the endothelium acts as a selective barrier between the vessel lumen and surrounding tissue, controlling the passage of materials and the transit of white blood cells into and out of the bloodstream. A critical feature of the engineered structures is that they recapitulate the native architecture, which includes an endothelium lining.

Collagen matrices will be seeded with 2 million endothelial cells and maintained in medium containing DMEM, 10% horse serum, 1% antibiotics, and 25 mM HEPES and allowed to culture for a minimum of 72 hours and a maximum of 2 weeks. Standard confocal and western blotting approaches (detected using ECL (Amersham)) will then be used to qualitatively and quantitatively assess proliferation, apoptosis, cell phenotype and cytoskeleton organization. 1) To assess proliferation of endothelial cells, cultures will be labeled for phosphorylated histone H3 (mAB, Cell Signaling Technology). 2) To assess apoptosis we will use immunohistochemistry for caspase-3 followed by morphometric point counting. Caspase 3 will also be quantitatively assessed from Western blots. 3) To assess phenotype, the cultures will be fixed in 4% paraformaldehyde. After fixation, the tissue sample will be vibrotome sectioned for confocal immuno-microscopy for PECAM (Sigma, vascular endothelial cells), isolectin (blood vessels), and for the extracellular matrix markers collagen 1 (Chemicon, Inc) and periostin (AbCam) using standard protocols. 5) Finally, cell junctions will be stained for connexin 43 by primary antibodies (anti-connexin 43 mAb, BD Biosciences; 1:100). Antibodies will be localized in the cells using Alexa fluor-conjugated secondary antibodies and counter stained with 0.1% propidium iodide to label nuclei. Confocal imaging will be carried out using a Ziess laser scanning confocal microscope (LSCM) using standardized settings.

Example 4.2: Culture Bone Marrow Stromal Cells on Both the Cast and Electrospun Scaffolds Another way to recapitulate the in vivo characteristic lining of the vasculature system is by introducing bone marrow stromal cells. The bone marrow stromal stem cells (also called mesenchymal stem cells or skeletal stem cells) can differentiate into bone, cartilage, fat, fibrous connective tissue, among others. As can be seen from our published manuscripts as well as our preliminary data, we have been successful in our laboratory culturing BMSCs on various substrates. Working in collaboration with Valarmathi et al. we used bone marrow stromal cells in our 3D tubular collagen scaffold, which was able to support vasculogenic differentiation producing microvascular structures. This is characteristic of the post natal de novo vasculogenesis. The BMSCs can mature and differentiate into endothelial and smooth muscle lineages. The potential of the 3D structure allows the study of the conditions that contribute to the differentiation with respect to architecture, dimensions, amount of cell receptors, and substrate composition. By incorporating BMSCs into the collagen hydrogels, we will obtain important information as to how the scaffold features influence the differentiation and cell biology of pluripotent cells.

Our preliminarily data, shown in FIGS. 10a-10d, is based on seeding the collagen hydrogel cast channels with bone marrow stromal cells in order to analyze the influence of the niche in the differentiation of the stem cells. The bone marrow stroma cells were isolated from the rat's tibia, femur, and fibula and passaged three times to eliminate differentiated cells. The remaining cells were mesenchymal stem cells are multipotent stem cells.

Experiments in this example will focus on evaluating the cell biology of the BMSCs cultured on our novel scaffolds. The experimental materials used here will include isolated bone marrow stromal cells as described. Collagen matrices will then be seeded with 107 BMSCs and maintained in differentiation medium containing DMEM, 10% horse serum, 1% antibiotics, and 25 mM HEPES and allowed to culture for a minimum of 72 hours and a maximum of 2 weeks. Standard confocal and Western blotting approaches (detected using ECL (Amersham)) will then be used to qualitatively and quantitatively assess proliferation, apoptosis, cell phenotype and cytoskeleton organization. 1) To assess proliferation of BMS cells, cultures will be labeled for phosphorylated histone H3 (mAB, Cell Signaling Technology) 2) To assess apoptosis we will use immunohistochemistry for caspase-3 followed by morphometric point counting. Caspase 3 will also be quantitatively assessed from Western blots. 3) To assess phenotype, the cultures will be fixed in 4% paraformaldehyde. After fixation, the tissue sample will be vibrotome sectioned for confocal immunomicroscopy for α-SMA (Sigma, vascular smooth muscle cells and myofibroblasts), isolectin (blood vessels), and for the extracellular matrix markers collagen 1 (Chemicon, Inc) and periostin (AbCam) using standard protocols. 5) Finally, cell junctions will be stained for connexin 43 by primary antibodies (anti-connexin 43 mAb, BD Biosciences; 1:100) and PECAM. Antibodies will be localized in the cells using Alexa fluor-conjugated secondary antibodies and counter stained with 0.1% propidium iodide to label nuclei. Confocal imaging will be carried out using a Zeiss 310 laser scanning confocal microscope (LSCM) using standardized settings.

Example B

Materials and Methods
BSA Rubber:
BSA (lyophilized and deionized powder, purity grade >98%, Sigma) and Glutaraldehyde (25%, Sigma) were used. Three solvents were used: 2×PBS, 1×PBS, and DI (deionized water). Pure water was used for making all solutions (Milli-Q, Millipore). The range of BSA concentration was 20%, 30%, and 40% wt. The glutaradehydye concentrations used were 2%, 3%, and 6% v/v. Table 1 lists the combination of BSA and glutaraldehyde tested. Using a 24 well plate (Corning), 1 mL of BSA mixture was added at the appropriate concentration and crosslinked it with 250 µL at the appropriate concentration of glutaraldehyde. They were left to react overnight at 4° C. in the molds. The next day, an 8 mm punch of each sample was obtained. For each concentration, 4 samples were made, and the testing was done in triplicates.

Compression Testing of BSA Rubbers:
To characterize the rubber, compressive testing was performed. Four samples were tested: 30% BSA and 3% Glutaraldehyde in 2×PBS, 30% BSA and 3% Glutaraldehyde in 1×PBS, 20% BSA and 3% Glutaraldehyde in 2×PBS and 20% BSA and 2% Glutaraldehyde in 1×PBS. Using the Bose Electroforce 3100 (Bose Corporation), three samples of each set were tested using a 5 lbf load cell. The displacement and load measurements were obtained having the load as the feedback. Five load cycles were performed using a sine wave compression. The stress and strain at each point was determined. The elastic modulus was obtained from the slope of the stress and strain curve in the elastic region.

Solids Content of the BSA Rubber:
A separate set of samples was used to quantify the percentage of dry solids in each of the BSA rubber samples shown on table 1. Using a 24 well plate (Corning), 1 mL of BSA mixture was added at the appropriate concentration, and it was crosslinked with 250 µL at the appropriate concentration of glutaraldehyde (table 1). They were left to react overnight at 4° C. in the molds. The next day, an 8 mm punch of each sample was obtained. The initial wet weight of the rubbers was determined, and then they were placed on the lyophilizer overnight. Then, the dry weight of the rubber was determined. This process was done in triplicates.

Enzyme Digestion:
The BSA rubber was enzyme digested using trypsin at pH 7.8 and temperature of 30° C. A 8 mm BSA rubber punch was placed on a 15 mL conical tube and the initial rubber weight was determined. 1 mL of 0.25% Trypsin in DI pH 7.8 at 30° C. was added. Samples were taken at 15, 24, 48, and 72 hr. On each time point, the supernatant was extracted, and the remaining rubber was lyophilized. To determine the total protein dissolved by the trypsin, a total protein assay was performed (Bicinchoninic acid assay, BCA, Pierce). The absorbance at 562 nm was obtained using multi-mode microplate reader (Biotel). BSA rubbers were exposed to 0.25% Trypsin solution (pH 7.8) at 30° C. The weight of the rubber was determined prior and after the enzyme treatment by lyophilizing the sample.

3D Mold:

To create a customized biodegradable rubber mold, 3D solid mold pieces were made that would hold the model dimensions. Using MasterCAM®, a solid was designed, and then the solid model was converted into machine G-code language. Once in G-Code, the program was then transferred to a Microlution 363-S micro milling machine to create the mold in stainless steel and brass. A so-called "Y Mold" was fabricated, and another mold called "Loop Mold" was fabricated using MakerBot Replicator2 3D Printer. Using the Replicator software, the program was imported into the 3D Printer. This printer has a 100 micron layer resolution and allows the fabrication of polylactic acid (PLA) molds by depositing layer by layer of this material to build the piece. A "stability piece" was also made, in which the fidelity of the smallest features was tested so that the process can be replicated with the BSA rubber.

BSA Rubber Molds:

The rubber is reaction injection molded into the intricate geometries of our tissue molds. Using an air brush sprayer (Air Brush Kit, Central Pneumatic), a release agent (Lard, Fields) was distributed on the surface of the mold. The sprayed molds were left to cool down for about 2 hr. The 30% BSA and 3% Glutaraldehye in 2×PBS solution were added to the dispenser (Medmix) in order to deliver 4:1 ratio respectively. The solution was reaction injected to the flowpaths to create the biodegradable rubber. The molds were left to react overnight at 4° C.

3D Collagen Scaffold:

The collagen was extracted by our previous published procedure[12]. After determining the solid percentage, the collagen was acidified and mixed to obtain the desired concentration. 4 mL of 1.75% collagen hydrogel was produced. The collagen hydrogels were mixed with 10 ug/mL of laminin[13]. To polymerize the collagen, 10× Minimum Essential Medium (MEM-Gibco) and 0.2 N HEPES (Sigma) at a pH 9 were added in an 8:1:1 ratio at 4° C. About half of the hydrogel was casted on a 12 well plate. The BSA rubber was placed on top, and was covered with the rest of the collagen. They were placed in 37° C. incubator for 1 hr. After the incubation period, the hydrogels were UV crosslinked using energy of 630000 micro joules per centimeter squared. The BSA Rubber was enzyme digested with 0.25% Trypsin solution. The BSA rubber was digested using this 0.25% trypsin solution with a pH of 7.8 and at 30° C. for 15 hr. After the 15 hr period, two sterile Mosconas washes were perform for 30 min each.

Results

Consistency and Mixability of the BSA Rubber:

The reaction time of the BSA decreased as the concentration of glutaraldehyde increased, as expected. The fixative reacts with the α-amino groups of the amino acids, the N terminal amino group, and the sulfhydryl cysteine group. The glutaraldehyde reacts predominantly with the bovine albumin serum through the amino groups of lysine to form the intermolecular covalent bonds. It is the crosslinks that give the protein a rubbery consistency. After incubation period, the samples showed a color change from pale yellow to dark yellow and brown, increasing in intensity with glutaraldehyde concentration. This color change is attributed to the formation of the aldimine linkages[15-17]. The 20%, 30%, and 40% BSA with 2% Glutaraldehyde in DI didn't form a rubber. Previous researchers have indicated the rapid reaction of the glutaraldehyde when placed in contact with the protein[18]. The 40% BSA solution, due to its high viscosity and the highly reactive fixative resulted on varying strength along the rubber. This behavior can be caused by the difficulty of the glutaraldehyde to penetrate the protein chains homogeneously. The solvent greatly influence the solubility of the protein as well as its reaction with the fixative. The 2×PBS solutions were easily mixable. The BSA solution with DI was difficult to mix. The bovine albumin serum solubility is greatly affected by ionic strength of the solvent (Table 2), causing conformational changes in the protein. The most promising samples were the 30% BSA with 3% Glutaraldehyde in 1×PBS and 2×PBS. Table 1 contains a brief visual description of the BSA rubber formation.

Compression Test on BSA Rubber:

The mechanical properties of four samples of BSA Rubber were measured: 30% BSA 3% Glutaraldehyde in 2×PBS, 30% BSA 3% Glutaraldehyde in 1×PBS, 20% BSA 3% Glutaraldehyde in 2×PBS, and 20% BSA 2% Glutaraldehyde in 1×PBS. The sine waves showed a very small phase change between the load and displacement curves that is transferred to the stress and strain curve. Based on the stress and strain curves, the first three samples show hysteris in between loading and unloading. These three specimens behave as a viscoelastic material that contains elastic and viscous properties when forces are applied to it. The 20% BSA 2% Glutaraldehyde shows signs of permanent deformation. The 30% BSA 3% Glutaraldehyde in 1×PBS and 2×PBS show a similar behavior. It was determined that the elastic modulus in the linear portion of these four samples. The amount of the glutaraldehyde and concentration of the phosphate solvent significantly increased the elastic modulus ($p=0.004$ and $p=0.003$, respectively). The BSA concentration did not contribute to the elastic modulus ($p>0.05$). The 20% BSA 2% Glutaraldehyde in 1×PBS deformed easily, showing lower elastic modulus.

Determination of Reaction Rate of the BSA Rubber Digestion:

The reaction rate was determined based on the disappearance of the BSA rubber caused by the enzyme digestion at each time point. The enzymatic digestion process was treated as a batch reactor. A comparison between the starting rubber concentration prior treatment and the rubber left after being lyophilized was made to obtain the kinetics of the digestion. The rate of reaction of each sample, in relation to the concentration of glutaraldehyde, BSA concentration, solvent, and the residence time was studied. A clear trend can be observed between the crosslinker concentrations to the reaction rate of dissociation of the entity. Statistical analysis was performed at each time point, which correlates the initial observation. For the 15 hr time point, the glutaraldehyde concentration significantly affected the reaction rate showing a p value of 0.02. After that time point, both the glutaraldehyde and BSA concentration significantly affected the rate. It was determined that the most influential factor overall was the glutaraldehyde concentration, indicated by a more significant p value. The increase of glutaraldehyde concentration decreased the reaction rate of the digestion of the rubber entity.

Quantification of Soluble Protein:

The amount of protein dissolved by tryspin was determined using BCA assay. The common trend was the lower the concentration of the fixative the more protein was digested for the BSA rubber. The trypsin interacts with the rubber sample, by cleaving the BSA and the newly created covalent bonds formed by the glutaraldehyde, dissolving the overall structure over time. It seems that with the 1×PBS we have more solubilized protein at an earlier time point compared to the 2×PBS samples. Over time, we can see an increased on proteins in solution at 15 hr, which continues to increase until 48 hr and then it decreases. This might be due to the trypsin constantly cleaving the proteins creating smaller peptides and amino acids. The BCA assay has some limitation in which it can only read peptides that are composed of three or more amino acids. Statistical analysis showed that the BSA and glutaraldehyde concentration significantly affected the release of the protein from the BSA rubber ($p<0.05$). An increase of BSA concentration caused an increase of protein in solution, while an increase in glutaraldehyde caused a decrease in dissolved protein.

Dissociation of the BSA Rubber:

The rubber was weighted (wet basis) before placing it in contact with the tryspin. We determined the equivalent of dry weight of the rubber placed in the enzyme digestion solution. The enzyme solution reacted with the BSA rubber, solubilizing the protein. The rubber left after the treatment was lyophilized overnight and weighted. It was found that the solvent influenced the dissociation of the rubber. At same concentration of BSA and glutaraldehyde, the 2×PBS solvent rubbers retain more their material compared to the 1×PBS.

3D Collagen Scaffold:

We fabricated three solid mold pieces: "Loop Mold", "Stability Piece", and "Y Mold". We obtained the stainless steel Y mold piece using the Microlution machine. This mold, was reaction injected with 30% BSA and 3% Glutaraldehyde in 2×PBS. The rubber was allowed to react overnight at 4° C. The rubber was casted with collagen and then enzyme digested. Our preliminary data suggests that at pH 7.8 and temperature of 30° C. for 15 hr, we can digest the BSA rubber with minimal impact on the collagen scaffold. After 15 hr, the rubber is loose enough and weakened by the enzyme that it leaves the channels without affecting the geometrical features of the collagen. We obtained a 3D collagen scaffold that had specific geometrical features, which had a 4 mm diameter channel inside a collagen hydrogel after enzyme digestion of the BSA rubber. We determined that we can create BSA rubber molds that have diameters as small as 300 um using the stability mold.

Discussion

Biofabrication is a highly multidisciplinary field in where biology and engineering principles need to be merged to generate complex materials that mimic the native tissue. In order to achieve this, we need to develop techniques that involve the implementation of the information gather from in vivo tissue and deliver all that directives into an in vitro scaffold. This way, we can engineer a platform that closely resemble architectural, function, mechanical and chemical stimuli, as well as the adequate cell population. The optimal scaffolding material should possess certain properties such as being compatible, immunogenic, nontoxic, capable of controlled degradation, support cell viability, and allows tissue remodeling.

Various fabrication techniques have been developed. Each technique has its pros and cons in advancing the new generation of the tissue scaffolds. Each technique needs to provide the material, geometrical features, and specific instructive characteristic of the tissue of interest. Most fabrication techniques based on creating specific geometries, fall under two categories: conventional and advanced. The conventional techniques include the use of synthetic and natural traditional materials to make porous structures. Some examples are solvent-casting, freeze drying, and melt molding. One of the disadvantages of these techniques is the poor control of porosity within the structure (pore size and pore interconnectivity) as well as its difficulty making internal channels within the scaffolds. Advanced techniques include sterolitography, molding, 3D printing, and electrospinning among others[1, 19]. Our technology incorporates both conventional and advanced fabrication techniques. The convergence of the computer aided manufacturing, in where we create or import the desired architectural features, and the development of an enzyme labile rubber, we take advantage of the best of both worlds. The negative molds milled using the architectural directives provided by the CAD program provides solid molds that after being reaction injected with the BSA rubber components, creates an easy and reliable transfer of the features to any material. This allows not only the control of external tissue composition, but also internal highly complex structure. The work presented here focus primarily on characterizing the BSA rubber. Our goal was to obtain a material that mixed homogeneously, digested in a reasonable amount of time, resistant to alterations in its structure, and able to mimic the smallest features while holding its stability. This assemble has to endure loading forces subjected by the casting material.

Serum albumin is the most abundant protein in the circulating system. Albumin is one of the longest known and most studied of all proteins, dating the research since the 1940s, where it became important at World War II as a stable blood substitute[20]. This protein is used in the biochemical and food industries[21]. Interesting, most of the research on solubility has focus on low concentrations of BSA in water. The solubility of the proteins is determined by intermolecular effects such as the protein-protein interaction but also the interaction with the solvent induces changes on the protein overall behavior. Since the protein are polyelectrolytes, solubility is determined by the electrostatic interactions[21]. Yadav et al showed the relationship between the viscosity and pH of at high protein concentration solutions, showing an altogether different behavior compared to dilute protein solutions. It was previously stated that the viscosity of the protein should be at its minimal at the isolectric point (pI-4.7), leading to viscosity increases as the pH moves away from the pI due to repulsion electroviscous effect[22]. At higher concentrations (250 mg/mL or 24%), he showed that the isoelectric point was the point of the highest viscosity caused by the attractive forces resulting in the protein self-aggregation. The viscosity decreases as the pH changes either to the acidic or basic side of pH 5 [23]. We saw in our study, the DI samples are closer to the isoelectric point compared to the PBS samples at higher concentrations (30% BSA), showing an increased in viscosity as previously stated. The viscosity of the BSA at high concentrations was highly reduced when we used the highest amount of salt in our solvent (2×PBS), while for the DI samples, the solutions was more viscous, specially at higher concentrations (40%). The conductivity was higher at PBS than DI solutions. The solvent can be inducing ionic interactions causing conformational changes on the intermolecular linkages, facilitating the solubility and mixability of the components. This is in agreement with previous researches that observe that the intrinsic viscosity of the protein decreases with increased in salt concentration until it reaches a asymptote at high salt concentrations[24].

Glutaldehdeye is a crosslinking agent that causes changes on the solubility of the protein. It's a compound that binds covalently to the amine group of lysine or hydroxylysine in the protein molecules, stabilizing the protein structure better than by aggregations attempts using solvents. Silva et al indicated that the number of free lysine group is important for the formation of the aggregates when using glutaraldehyde as the crosslinking reagent [18, 25]. Based on our data, the percentage of fixative improved the elasticity of the rubber (from 2% to 3%). The behavior of the ideal rubber (30% BSA 3% Glutaraldehyde in 2×PBS or 1×PBS) behaves as a viscoelastic material that can withstand loading without permanently deforming. This becomes very important when handling and casting material around this structure.

Trypsin readily digested the BSA rubber while leaving the collagen untouched. Trypsin is a serine protrase that hydrolyzes proteins. Trypsin is a widely used enzyme that has high cleavage specificity. It cleaves the peptides chains mainly at the carboxyl side of the amino acids lysine or arginine. It has been reported in literature that the long incubation periods produces nonspecific cleavage, deamination and oxidation and trypsin autlolysis products [26]. In our studies, the trypsin readily digested the BSA rubber leaving the collagen intact and relatively untouched. This demonstrates the efficacy of the BSA rubber as a sacrificial material for biofabrication.

Currently, a similar system called BioGlue is being used as a surgical adhesive. This sealant is composed of 10% glutaraldehyde and 45% bovine serum albumin. This material has been used for the treatment of aortic dissections, ventricular septal defects, pulmonary air leaks, hemorrhage, and reinforcement of synthetic grafts. One of the main concerns of using this glue is the release of free glutaraldehyde that may be delivered to the tissue. There is evidence supporting that the direct contact between the BioGlue and the phrenic nerve, causes nerve injury and even paralysis of the nerve [27]. Furst et al. showed that after the glue polymerizes and its place in contact with fluid, free glutaraldehyde is released, enough to become cytotoxic to cells [28]. In our studies, we use the BSA rubber as a sacrificial material to transfer the geometrical features to a scaffold material and release it as soon as possible. The material will not have any contact with cells. The construct will be thoroughly free of any BSA and glutaraldehyde material that can affect the in vivo behavior of cells.

Conclusion

This biofabrication technique is a step forward in the generation of in vitro scaffolds that can recapitulate the intrinsic geometrical features quickly and reliable way. We selected a natural material such as collagen because natural materials offer superior chemical and physical cues to cells. These materials can be used for therapeutic research, as in vitro models of development, malformed, and disease tissue, as well as replacement of damaged tissue.

Example C

A series of experiments were conducted to evaluate the reaction electrospinning and evaluate the state of the collagen fibers produced. Scanning electron microscopy (SEM) was used to determine the fiber diameter and transmission electron microscopy (TEM) to determine the banding pattern. Trypsin digestion assays were performed to determine the stability of the triple helical structure. This newly developed reaction electrospinning technique combines the fiber formation process of electrospinning and fibrillogenesis. The fibrils undergo fibrillogenesis and reprecipitate native banded collagen fibrils within the spun fibers. This method produced electrospun collagen fibers that contained an average periodicity of 65.4±2.6 nm that were resistant to trypsin digestion which indicates that the triple helical structure present in the native collagen structure is also maintained in the fibers. These fibers were compared with fibers produced by conventional electrospinning methods. Fibers spun from solvent based systems did not have the characteristic banding pattern nor where they resistant to trypsin digestion.

The majority of human tissues and organs are attached to a collagen fibrous structure with a fiber size ranging from the nanometer to millimeter scale. Electrospinning is currently the most successful method for the fabrication of nanofiber structures. Unfortunately, common solvents have been found to affect the collagen structure. This study showed a new technique called collagen reaction electrospinning to produce scaffolds that are biocompatible, supporting a submicron fibrous platform for the use of tissue engineering and regenerative medicine. The fibrous nanoscale structures made of a clinically approved biopolymer provides the necessary support for cells allowing them to demonstrate typical in vivo behaviors. The similarities between the electrospun collagen fibers and the morphology of the ECM provides an ideal biomimetic niche for seeded cells. Using electrospun fibers researchers have labored to replicate several tissue morphologies including cartilage, bone, vasculature, and nerves.

The development and optimization of the reaction electrospinning procedure is generally provided herein. This technique combines electrospinning with the fibrillogenesis process. Monomeric native molecules and intermediate aggregates are soluble and stable at pH 3 at a low ionic strength and temperature. The acidified polymer solution is used as our electrospinning solution. As the collagen solution is electrospun, there is an increase in the temperature and pH caused by contact with the ammonia vapors and solution. This initiates the self-assembly fibrillogenesis process. The aggregation process initiates with a quarter-staggered arrangement of the monomers, which then aggregate into five-stranded fibrils that continue to further assemble to form larger fibrils. In this process, the diameter of the fibers can be controlled as they are being precipitated and reconstituted into collagen fibrils that resemble the behavior of native collagen.

Several parameters affect the fibers created by electrospinning. These include the solvent, solution viscosity and conductivity, the strength of the field, the flow rate, and the air gap (the distance between the collector and the syringe tip). The most common types of solvents used for electrospinning are the fluoroalchohols that reduce the surface tension of the solution. Common electrospinning procedures use 3%-10% collagen solubilized in HFP. Matthews et al. found no evidence of electrospinning at a collagen concentration of 0.0083 g/mL (0.8 wt %). Failure to electrospin might be caused by the effects of the fluoroalcohols on the collagen. A collagen range was selected from 1-2.5% collagen, which is lower than previously published data, and acidified collagen was used dissolved in ethanol. This solution contains a combination of monomers and microfibrils. At lower concentrations, the necessary properties were realized to electrospin the collagen. Within the tested range we obtain non-soluble fiber formation at each collagen concentration. The collagen concentration is not correlated to fiber diameter within this range (p=0.368). The first set of experiments was designed to determine which parameters—including electrical field, air gap, flow rate, and gauge—affect the fiber diameter. Of these parameters only the electrical field and the flow rate affect the fiber diameter. Previous researchers have found that the concentration of the polymeric solution affects the fiber diameter. A second experiment was performed to determine the relationship between the collagen concentration and the fiber diameter. These experiments indicated that within this range, the collagen fiber diameter is affected by the field and flow rate and is independent of the collagen concentration.

Collagen in its native state and under physiological conditions is a water-insoluble polymer due to its hydrophobic residues residing on the outside of its polypeptide structure. HFP solubilizes the collagen, but in the process the two trifluoromethyl groups break the hydrophobic interactions and the solvent's acidity assists in breaking the hydrogen bonds. The electrospun collagen scaffolds made out of the fluoroalcohols are soluble in aqueous media. The shift from a water insoluble protein to a water soluble protein entails conformational changes in the protein structure due to damage to their secondary structures. This results in fibrous structures that are not suitable for use as tissue engineering scaffolds. To compensate for this, researchers have used several crosslinking mechanisms to stabilize the structure of the electrospun fibers. One of the most common crosslinking reagents is glutaraldehyde. Glutaraldehyde reacts with the amide group of collagen forming crosslinks between the polymer chains, but this approach introduces toxicity, side products, and changes in morphology (porosity and fiber diameter). Dong et al. shows that by using a benign solvent that combines water and ethanol with salt, collagen can be solubilized at a neutral pH, creating a stable electrospinning system. The collagen mats produced are still soluble and additional crosslinking with 1,ethyl-3(3-dimethylaminopropyl)carbodiimidehydrochloride) (EDC) and N-hydroxysuccinimide (NHS) is required. The high concentration of salts destabilizes the collagen, which can cause conformational changes in the protein. This study showed that using conventional electrospinning experimental procedures, the collagen fibers produced were soluble in PBS. The RE collagen fibers were not soluble in water even before crosslinking them. In contrast to other crosslinking methods, the fibers were UV irradiated to reconstitute the covalent bonds existing in the native collagen structure, and the collagen fibrils closely mimic what is observed in the native tissue. UV irradiation stabilizes the collagen structure and improves its mechanical properties without adding toxic chemicals, making the structure resistant to enzymatic attack.

One of the most important features of reconstituted collagen fibers is the characteristic D banding. This pattern, which results from the alternating overlapping and gap zones caused by the specific assembly arrangement of the collagen molecules, is called the "fingerprint" of collagen. Fibrillogenesis, or the process by which collagen molecules assemble into collagen fibers, is governed by covalent bonds, electrostatic forces, hydrophobic, and hydrophilic interactions. Previous researchers have shown that the characteristic banding pattern is affected by factors such as the buffer type, ionic strength, and pH affecting the in vitro fibrillogenesis process. As indicated before, the most common solvents for electrospinning are fluoroalcohols which has been shown to affect the molecular structure of proteins. Previous publication has shown that the triple helical structure of collagen is denatured when using these solvents. TEM images of CE collagen fibers shows a loss of this characteristic banding patterns due to the interaction with the fluoroalchohol, which is an indication of denaturalization of the collagen structure that correlates with previously published data. The RE collagen fibrils maintain the characteristic banding pattern that closely resemble the range of the individual fibrils found in biologically derived collagen. The ability of collagen to form striated fibrils involves hydrophobic and charge interactions. Researchers have argued that in order to fully characterize the fiber diameter, analysis by TEM and SEM should be employed, based on the limitations of each technique. SEM is unable to detect objects smaller than 0.25 µm, but TEM cannot detect fibers larger than 60 µm. The size distribution of the RE collagen fibers is 100-500 nm. This range is close to ideal, mimicking the native ECM (50-500 nm).

Tissue engineering scaffolds need to demonstrate that they are biocompatible and that cells shown in vivo like behaviors. Kyong et al. showed relatively low cell adhesion of keratinocytes in uncoated electrospun collagen fibers using conventional methods. This can be cause due to the changes in the adhesion sites due to the denaturalization of the protein. Another possibility is that due to the strong crosslinking effects of the glutaraldehyde, the porosity of the construct is reduced, preventing the cell's ability to grow deep into the scaffolds. There was an increased cell adhesion when these fibers were coated with collagen. As revealed by immunostaining of $\alpha$-smooth muscle actin and CD31, myofibroblast and endothelial cells adhere to the collagen fibers and maintain their phenotypic expression. There are also signs of contraction of the matrix and common endothelial cell behaviors including forming small clusters of cells and creating sprout extensions on the constructs cultured for longer periods of time.

Additionally, the tight triple helical structure of the collagen is resistant to pepsin and trypsin, unless the structure is compromised. Trypsin is the most recognized enzyme to identify the structure integrity of collagen. Following previously published electrospun methods, collagen and gelatin were dissolved in HFP. The CE collagen fibers were soluble in trypsin. These fibers were not exposed to glutaraldehyde prior performing the assay. Immunoblot analysis shows that there is little protein dissolved when the RE collagen fibers are subjected to trypsin digestion. This protein can be attributed to a small amount of loosely packed collagen.

Conclusion

Reaction electrospinning produces collagen fibers that can be reconstituted into mature collagen fibers. Using benign solvents, we eliminate the toxicity attributed to previously established procedures without denaturing the collagen fiber structure. Using this design, we can obtain a triple helical collagen desired to generate fibrous collagen scaffolds.

2. Materials and Methods 2.1 Fiber Fabrication Though Reaction Electrospinning

An electrospinning apparatus was built, and a high-voltage power supply (Spellman CZE 1000R, Spellman High Voltage Electronics Corp., Hauppauge, N.Y., USA) was used to charge the polymeric solution, which is contained in a syringe. The syringe was connected so that at the tip of the needle or nozzle delivers a charged polymer jet. The collection target which is a conductive solution was electrically grounded. For this setup the collection target was stationary, providing a random fiber orientation. Previous researchers have used several collectors, such as mesh screens, by using either a rotational or stationary mandrel to impart varying degree of fiber orientation. The syringe and syringe pump motor (Digital Servo Motor, Emerson Industrial Automation, Control Techniques Americas, LLC, Eden Prairie, Minn., USA) were placed vertically and driven by a Epsilon EP 204 (Emerson Industrial Automation). This allowed the controlled delivery of the optimal volume at a controlled volumetric-flow rate to cover the collection target.

The collagen was extracted from steer hide using a method previously described. The collagen solution was adjusted to a pH of 3 using very small amounts of 12M HCl, incubated at 4° C. overnight, and checked the next day. The collagen was then diluted with DI water to the desired collagen concentration. The solution was further diluted with 70% ethanol to create a 1:1 EtOH:H$_2$O mixture and acidified to pH 3. The solution was aliquotted into 3-cc syringes and briefly centrifuged to remove air bubbles. The syringe piston was then replaced and adjusted to the 3-cc mark on top. A 26-gauge needle (BD PrecisionGlide, BD Biosciences, San Jose, Calif., USA) was used.

The collector target included a glass tissue culture plate containing the collection solution of 8 M ammonia sulfate solution at pH 8 adjusted using ammonia gas. A nylon mesh was placed in the solution to recover the fibers. The solution was grounded to create an electrical field. A 12 gauge copper wire was grounded to the building at one end and the other in the ammonia solution to produce a grounded target. The positive wire from the power supply was connected to the syringe tip by an alligator clip.

Using a Power Tools Pro v5.1 (Emerson Industrial Automation), the shaft was jogged until it touched the piston. Controlled dispensing rates were programmed into the Servo motor controller. In the first experiments, a 2% collagen solution was used and the parameters for the electrical field, flow rate, gauge, and gap distance were varied (Supplemental Table 1). In the second set of experiments a 1% and 2.5% collagen concentrations were used with a 24-gauge needle and a gap distance of 7 cm and varied the electrical field and the flow rate (Supplemental Table 2).

Acidified collagen was dispensed at a controlled rate and simultaneously exposed to ammonia vapor and electrical field in a closed chamber. The spun fibers were collected in the stationary and grounded collection target as desired. The chamber was filled with a 50/50 mixture of nitrogen/ammonia gas for 30 min. The reaction electrospun (RE) collagen fibers were removed from the solution and placed in 4° C. DI water for 15 min. This process was repeated three times and the collected fibers were refrigerated overnight at 4° C. The following day, the fibers were washed three times more with 4° C. DI water for 15 min and then placed in a 0.3% bicarbonate solution for 15 min. The fibers were submerged in 4° C. DI water for 2 hr and placed overnight at 4° C. in a Mosconas solution (136.8 mM NaCl, 28.6 mM KCl, 11.9 mM NaHCO$_3$, 9.4 mM glucose, 0.08 NaH$_2$PO$_4$, pH 7.4; Sigma-Aldrich, St. Louis, Mo., USA). The fibers were then UV irradiated with 6.3×10$^5$ microjoules per cm2, and the fibers were divided into samples for SEM, TEM, trypsin digestion, and measurement of dry weights.

2.2 Conventional Electrospun (CE) Collagen and Gelatin Fibers

Using the methods described previously, lyophilized collagen from calf skin (Sigma, 83 mg/mL) and gelatin (Sigma, 110 mg/mL) were solubilized by vortexing for 12 hr in 1,1,1,3,3,3-hexafluoro-2-propanol (HFP) and electrospun. Following previous published experimental methods, the solutions were charged to 25 KV and delivered (0.08 cc/min) though an 18 gauge syringe across an air gap of 115 mm. The fibers were recovered on an aluminum foil sheet that had a grounded copper wire rack underneath it.

2.2 SEM

To determine the diameter of the RE fibers, samples were prepared for scanning electron microscopy (SEM). The method used was the GTA-O-GTA-O-GTA-O method. Fibers were fixed with 2.5% glutaraldehyde in DI water at 4° C. overnight. The sample was washed twice with 1×PBS. Samples were treated with 1% tannic acid/1% glutaraldehyde for 1 hr. The samples were immersed in a 1% aqueous solution of OsO4 for 1 hr. Samples were rinsed and treated twice with the GTA-O steps: 1-hr incubation in 1% glutaraldehyde/1% tannic acid at room temperature, followed by a 1-hr rinse in 1% OsO4. The fibers were then dehydrated in a graded ethanol series, dried to the critical point, mounted on aluminum stubs, and imaged on a JEOL (Tokyo, Japan) JSM-6300V at 10 KV. Using Image J software (NIH, Bethesda, Md., USA), we placed a grid on the images and selected nine intersection points, selected random fibers, and measured the fiber diameters. We calculated the mean and standard deviation (SD) per run.

2.3 TEM

To determine the molecular structure of the fibers, the samples were fixed with 2.5% glutaraldehyde in DI water at 4° C. overnight. The samples were washed twice with 1×PBS, and then immersed in 1% tannic acid/1% glutaraldehyde in 1×PBS for 30 min. After rinsing, samples were treated with 1% osmium tetroxide/1.5% K+ ferricyanide in 1×PBS for 1 hr. The samples were rinsed and dehydrated in a series of ascending aqueous ethanol concentrations. Samples were embedded in PolyBed 812. Ultra-thin sections were obtained using the Reinchert Ultracut E ultra-microtome (Leica Microsystem Ltd, Wetzlar, Germany) collected on copper grids. Contrast was added to samples with 2% uranyl acetate (aq) and a Hanaichi lead stain and imaged using a JEM-200CX transmission electron microscope (JEOL Ltd, Tokyo, Japan) at 120 KV.

2.4 Trypsin Digestion

To determine the integrity of the collagen, a trypsin digestion test was performed. RE and CE collagen fibers were exposed to a 0.25% trypsin solution (pH 7.8) overnight at 30° C. Briefly, the dry weight of the collagen was determined and place in a 50 mL conical tube that contained 4 mL of trypsin solution. The supernatant was extracted and a bicinchoninic acid assay (BCA, Pierce Chemical, Rockford, Ill., USA) was performed to quantify the amount of protein in solution.

2.5 Sodium Dodecyl Sulfate-Polyacrylamide Gel Electrophoresis (SDS-PAGE)

The supernatant of the trypsin digestion samples were taken to identify the proteins in solution for the RE collagen fibers. Three samples were taken from three independent fiber samples. 10 µg of protein were mixed with 10× protein loading buffer (1 M Tris-HCl, pH 6.8, 10% SDS, 0.2% bromophenol blue, 25% β-mercaptoethanol, and 50% glycerol) in a 9:1 (sample:sample buffer) ratio. Samples were run using 1× running buffer made from 10× Tris/Glycine/SDS Buffer (Bio-Rad Laboratories, Hercules, Calif., USA). The samples were heated for 5 min at 95° C. After being heated, 40 µL of each sample was loaded in the wells of a 4-20% Mini Protean TGX Gel (Bio-Rad Laboratories), and electrophoresis was performed at 100V. After electrophoresis, the gel was fixed with a mixture of 50% (v/v) methanol and 10% (v/v) acetic acid for 30 min at room temperature, followed by staining with 0.01% (w/v) Brilliant Blue R-250 (ThermoFisher Scientific, Waltham, Mass., USA) in 20% (v/v) methanol and 10% (v/v) acetic acid overnight in a shaker at 4° C. Finally, the gel was destained by washing three times with a mixture of 30% methanol and 10% acetic acid for 30 min each in a shaker at 4° C. Precision Dual Color Standards (Bio-Rad Laboratories) was used to estimate the molecular weight of the protein. Each band was analyzed using Image J software to quantify the ratio of expression relative to other bands within each sample.

2.6 Western Blot Analysis

To determine the quantities of collagen in the trypsin assay of the RE collagen fibers, immunoblots were performed. The supernatants were obtained from the three independent samples of collagen fibers digested with trypsin. 10 ug protein samples were mixed with 4× Laemmli sample buffer (Bio-Rad Laboratories) containing 100 mL/L β-mercaptoethanol (βME) in a 3:1 (sample:sample buffer) ratio. Samples were run using 1× Buffer made from 10× Tris/Glycine/SDS Buffer (Bio-Rad Laboratories). The samples were heated for 5 min at 95° C. After being heated, 40 μL of each sample that contained 50 μg of protein was loaded in the wells of a 4-20% Mini Protean TGX Gel (Bio-Rad Laboratories), and electrophoresis was performed at room temperature at 100V. The proteins were transferred to membranes in electroblot transfer buffer (25 mM Tris, pH 6.8, 190 mM glycine, and 20% methanol) at 100V and 4° C. for 80 min. The blots were blocked in 5% nonfat milk in washing buffer (20 mM Tris, pH 6.8, 137 mM sodium chloride, and 0.2% Tween 20) for 1 hr at room temperature. Subsequently, they were exposed to anti-collagen I antibody (Novus Biological, NB600-408, Littleton, Colo., USA) at 1:1000 overnight at 4° C. Then, we added a goat anti-rabbit IgG horseradish peroxidase secondary antibody (G2123, Invitrogen, Eugene, Oreg., USA) at 1:5000 for 1 hr at room temperature. The blot was washed on an orbital shaker for 30 min, changing the washing buffer every 10 min. To detect the bound antibodies, we used an enhanced chemiluminescence detection system (Pierce ECL Western Blot Substrate, Rockford, Ill.). Images were taken at an 8-min exposure.

2.7 Cell Culture

Cells were cultured in 75 cm2 BioLite culture flasks (ThermoFisher Scientific) at 37° C. in 5% $CO_2$ humidified incubators. Human adipose microvascular endothelial cells (HAMEC; ScienCell Research Laboratories, Carlsbad, Calif., USA) were grown in Endothelial Cell Growth media (EGM-2; Lonza Group Ltd., Basel, Switzerland). Adult normal human dermal fibroblast cells (NHDFs, Lonza Group Ltd.) were cultured in Fibroblast Growth Media (FGM-2; Lonza Group Ltd.). The cells were passaged using 0.05% trypsin in 1×PBS (ThermoFisher Scientific) and harvested when they reached a confluency of approximately 80%.

2.8 Generation of RE Collagen Constructs

Reaction electrospun collagen fibers were seeded with fibroblasts and endothelial cells. We used a 4:1 ratio of normal human dermal fibroblasts (NHDFs) and human adipose microvascular endothelial cells (HAMECs), which has been reported to be the ideal ratio to promote vasculogenesis. Briefly, we used approximately 18 g of 2.5% electrospun collagen fibers spun at 20 KV at a flow rate of 0.5 cc/min. The fibers were placed in each well of a 12-well plate and seeded with a total of 1.5±0.5 million cells. The media used was a 2:1 ratio of Fibroblast Growth Media (FGM-2) and Endothelial cell Growth Media (EGM-2). The construct was incubated in cell culture for 2 and 5 days, changing the media after 3 days.

2.9 Immunofluorescence Labeling

The RE collagen constructs were washed with PBS and fixed with 4% paraformaldehyde for 1 hr at room temperature. The sample was washed with PBS and placed on a 12-well plate. The construct was permeabilized using 0.01% Triton X-100/0.01M glycine for 30 min and blocked with 5% BSA solution in 1×PBS overnight at 4° C. The anti-CD-31 (abcam, Cambridge, Mass., USA, 1:50) and anti-collagen 1 (abcam, 1:200) primary antibodies were diluted in a 1% BSA solution and incubated overnight at 4° C. After rinsing, the constructs were incubated for 2 hr at room temperature with Alexa Fluor 546 goat anti-rabbit (Molecular Probes, Eugene, Oreg., USA, 1:500), Hoechst 33342 (Invitrogen Life Technologies, Carlsbad, Calif., USA, 1:1000), monoclonal anti-actin, α-smooth muscle actin-FITC (αSMA; Sigma-Aldrich, 1:200), and Alexa Fluor 633 Phalloidin (Molecular Probes, 1:500) antibodies. Samples were mounted on glass slides with 1-mm coverslips using ProLong Gold antifade reagent (Molecular Probes).

2.10 Imaging

Z-stack images were taken (step size averaging 5 μm) using a Leica TCS SP5 AOBS Confocal Microscope System (Leica Microsystems, Inc., Exton, Pa., USA) in sequential multichannel mode. The stacks were projected at maximum and leveled using ImageJ and Adobe Photoshop CS5 (Adobe Systems Inc., San Jose, Calif., USA).

2.11 Statistical Analysis

Data presented are expressed as the mean±standard deviation (SD). One way analysis of variance (ANOVA) for multiple comparisons was employed to determine the variance of the population of the samples. The threshold for statistical significance was set at $p<0.05$. A Modified Thompson Tau test was used to determine outliers.

3. Results 3.1 Determination of the Parameters Affecting the Fiber Diameter

SEM micrographs of the RE collagen fibers were obtained. For each set of experimental conditions, a random fibrous mesh was created with average fiber diameter of 560±167 nm. The collagen concentration was constant at 2%. Fiber diameters of 625±81 and 644±61 nm were produced by 1% and 2.5% collagen concentration, respectively (RE Parameters are in Supplemental Table 2).

Using Design Expert® (Start-Ease Inc., Minneapolis, Minn.), an experiment of 22 runs was designed. Regression analysis and showed that there was a significant difference in the fiber diameter produced depending upon the flow rate ($p=0.046$) and the electrical field ($p=0.009$). These two parameters were the major factors that determined the fiber diameter of the collagen; whereas, the remaining parameters had minor or insignificant effects on the outcome ($p>0.05$). By removing the gap and gauge parameters from the statistical analysis, these findings became more significant. Because viscosity has been reported to play a role in the electrospun fiber, we designed a second set of experiments using two different collagen concentrations and varied the electric field and the flow rate. For this reaction electrospinning setup within the range of each parameter tested, we concluded that the electric field ($p=0.05$) and the flow rate ($p=0.048$) were the only variables that significantly influenced the electrospun collagen fiber diameter.

3.2 Determination of the Structure in the Electrospun Fibers

The reaction electrospun (RE) collagen fibers exhibit the characteristic cross striation pattern of native collagen independent of the collagen concentration. TEM images showed clear banding patterns of approximately 65.4±2.6 nm in width. The final run, which correlated to the lowest concentration, lowest flow rate, and highest electric field, produced the least associated collagen fibrils. This last run (Run 8) banding measurement was considered an outlier. An average periodicity of 67 nm is present in the native hydrated state. The preparation process that is composed of dehydration and shrinking has been shown previously can cause lower values on the TEM images ranging from 55-65 nm. These parameters produced a combination of predominantly fully assembled fibrils as well as a lesser amount of loosely packed collagen bundles. TEM showed that individual fibrils have a diameter of 145±33 nm.

The electrospun collagen dissolved in fluoroalchols showed a very different structure. TEM images of the CE collagen fibrils show no banding pattern, showing a very similar structure as the electrospun gelatin images.

3.3 Determination of the Integrity of the Collagen Fibers

Three independent samples were taken of the reaction and conventional electrospun fibers incubated with trypsin, and the amount of protein dissolved was determined by a BCA assay.

Using SDS-PAGE, the majority of the soluble protein was identified as trypsin, accounting for 75%, 72%, and 64% of each sample, respectively. The immunoblot analysis for the RE collagen fibers showed that there was very little protein dissolved during the trypsin digestion assay that corresponded to collagen. All three samples showed a faint band at approximately 60 KDa, which corresponded to hydrolyzed collagen. This is attributed to unraveled collagen fibrils which are susceptible to trypsin attack to a certain degree. The reaction electrospun collagen fibers were mostly resistant to trypsin digestion with a very negligible amount of 6.8% soluble collagen compared to the overall sample.

Fluoroalcohol electrospun collagen fibers showed a different outcome. The fibers subjected to trypsin digestion were mostly dissolved. Another set of samples was taken and place in phosphate buffer solution (PBS) to determine its stability. At room temperature, the mats turn from a white to clear structure, in which they remained relatively stable until incubated at the same conditions as trypsin. The dissociation of these fibers was 95% in trypsin and 63% in PBS.

3.4 Cell Adhesion to the RE Collagen Constructs

To determine the biological compatibility of the RE collagen fibers, we cultured endothelial and fibroblast cells for 2 and 5 days. Immunostaining was performed using three markers: collagen 1, α-smooth muscle actin (myofibroblast cells), and CD31 (endothelial cells). Immunohistochemistry confirmed the presence of these markers on the collagen fibrous scaffolds. Cells were also stained with Hoechst (nuclei) and Phalloidin (f-actin, cytoskeleton).

The immunostaining of endothelial and fibroblast cells after culturing for 5 days on collagen nanofibers showed that cells organized into cluster of cells with sprouting projections extending to another cell cluster—a behavior characteristic of endothelial cell sprouting. Collagen I has been shown to cause endothelial cells to assume a spindle-shaped morphology, which is similar to precapillary formation, and to align into cord assemblies. Microscopy analysis showed a fiber diameter averaging 450 μm, which indicated some reduction from the original fiber diameter (574 nm). In other areas of the sample, the fiber diameter averaged 1 mm in width, which might indicate merging of two fibers due to cellular contraction.

Example D

An innovative biofabrication technique was developed to engineer three-dimensional constructs that resemble the architectural features, components, and mechanical properties of in vivo tissue. This technique features a newly developed sacrificial material, BSA rubber, which transfers detailed spatial features, reproducing the in vivo architectures of a wide variety of tissues.

The prototype described in this Example uses the custom made stainless steel Y mold piece of FIGS. 3a and 3b. The mold contains an inflow and two outflow channels of 4 and 3 mm, respectively. First, clean molds, spray them with unsaturated lard, and sterilize them. Prepare the molds following the procedure described below.

1.1) Clean stainless steel molds using sonicator at a frequency of 35 kHz. Place the molds in the sonicator and submerge them with water and ice. Keep the molds cold at all times while the sonicator is running Run the sonicator for 2 periods of 90 min.

1.1.1) After each period, use a needle to make sure that there is no material in the luer lock stainless steel or brass connector. Use soap and water to clean the entire surface of the two sides of the molds. Verify that there is no obstruction in the channels.

1.2) Place the molds, screws, and luer lock connector in an autoclave bag and autoclave it.

1.3) Fill the bottle that attaches to an air sprayer half way with commercially available lard (mixed fatty acid release agent). Replace the cap with a regular cap bottle. Place it in an autoclave bag and autoclave it.

Note: Lard is used to facilitate the release of the material that will be reaction injected later on (BSA rubber). Do not place the sprayer bottle lid in the autoclave—it can damage the internal seal.

1.4) Warm up the lard for 45 seconds or until its clear and liquid in a microwave. Screw the air sprayer lid to the lard bottle. Connect the lid with the sprayer. Attach the sprayer to the air source at the lab bench. Open the air valve, and open the nozzle of the sprayer until it starts wetting the surface of a paper towel.

1.5) Spray lard perpendicular to the mold surface until the surface is fully covered. After each piece has been sprayed, place them in a petri dish and seal it. Place the molds at 4° C. for 2 h.

1.6) Proceed to sterilize the molds by exposing the surface to UV light for 30 min. Place them back at 4° C. until they are ready to be reaction injected.

2) Reaction Injection of the BSA Rubber

Note: All the materials and solution should be keep cold until ready to use to prevent premature setting of the BSA rubber in the next steps.

2.1) Prepare the dispenser for delivering the BSA rubber to the molds following these steps.

2.1.1) Sterilize all of the mixing components (two O rings, syringe cap, double syringe, mix tip, and 4:1 dispenser) by exposing them to UV light for 30 minutes in the polymerase chain reaction (PCR) hood.

Note: A PCR hood was used because this procedure involves fixatives. These chemicals cannot be used in the cell/tissue culture hood due to the risk of exposure and toxicity to the cells. Any other hood that contains a UV light will be suitable.

2.1.2) Place the tip cap on the solution holder.

2.1.3) Perform the mixing and injection at a 4:1 ratio of BSA:Glutaraldehyde. Add the 30% BSA to the double syringe chamber that will deliver the highest amount of solution (It will take approximately 4 mL to fill). Make sure to leave enough space to place the O ring in order to prevent overflowing and contamination of the adjacent chamber.

2.1.4) Add 3% glutaraldehyde solution to the other chamber (It will take about 1 mL to fill). Make sure to leave enough space to place the O ring to prevent overflowing and contamination of the adjacent chamber.

2.1.5) Place the double syringe on the dispenser. Tilt the assembly vertically so that the syringe cap is on top. Replace the cap with the mixing tip.

2.1.6) Screw the two stainless steel mold pieces together.

2.1.7) Place the assembly inside of an autoclave bag.

2.1.8) To remove any air in the dispenser, hold it in the upright position and quickly squeeze the handle one time to release a small amount of the BSA mixed with the glutaraldehyde. Then quickly attach the stainless steel Y mold's luer lock connector to the syringe tip.

2.1.9) Hold the stainless steel Y mold with the left hand and the BSA-Glutaraldehyde mixture dispenser on the right. Alternate covering each of left and right exhaust of the outflow channels by pressing the exhaust to the sides of the autoclave bag to make sure the inside voids are filled with solution. Then, place the molds horizontally and inject again.

2.1.10) Detach the molds from dispenser and place in a 25 mm petri dish.

2.1.11) Place parafilm around the Petri dish to prevent dehydration of the rubber.

2.1.12) Place the mold in the 4° C. fridge overnight.

3) Adjusting the Collagen Concentration

Note: The collagen should be kept on ice at all times during the process.

3.1) Modify the collagen concentration using the percentage of collagen solids.

3.1.1) Make 10 mL of 1.75% collagen by adjusting the initial collagen concentration with cold water.

3.1.2) Using a calibrated pH meter, adjust the pH to 3 using 12 N Hydrochloric Acid. Do not add the hydrochloric acid directly to the collagen—add the acid to the side of the tube. After adding the acid, use the spatula to push the acid into the collagen and quickly stir the mixture.

3.1.3) Weigh 4 g of collagen in a separate conical tube.

3.1.4) Centrifuge the collagen to remove air at 4° C. and 9343×g for 20-30 minutes.

3.1.5) UV sterilize the cell culture hood for 30 minutes, and add 14 μL of laminin to the 4 mL collagen. This will result in a final laminin concentration of 10 μg/μL. Note: Laminin provides structural integrity, adhesion, and promotes various cellular responses.

3.1.6) Turn the PCR UV light on for 20-30 min prior to using the hood for sterilization.

3.1.7) Place the luer lock cap, to attach to a 20 mL syringe, in ethanol for a 2 hr. Then, allow it to dry and place it in UV light.

3.1.8) Gamma irradiate the collagen for 8.6 min to reach 1200 cGy. (Note: The time will depend on the decay of the Cesium source. Adjust the time to reach the same dosage)

4) Casting Collagen on BSA Rubber 4.1) To polymerize the collagen, use an 8:1:1 ratio (collagen: HEPES:MEM). The following procedure is based on an initial 4 g of acidified collagen (From Step 5.1.8).

4.1.1) Make a 0.2 N HEPES solution in water, and adjust the pH to 9 by adding small amounts (1-5 μL) of 1-5 M sodium hydroxide (NaOH) solution. Using a calibrated pH meter, monitor the pH of the solution after each addition. Store at 4° C. or keep on ice.

4.1.2) Turn on the UV light of the tissue culture hood for 20-30 min to sterilize the hood.

4.1.3) Autoclave forceps, spatula, and scalpel for sterilization.

4.1.4) Mix 1.5 mL of 0.2 N HEPES (pH 9) and 1.5 mL of 10×MEM using the tissue culture hood. Make sure to keep it on ice and vortex it for 5 sec prior to use. Store at 4° C. or keep on ice.

4.1.5) To sterilize the PCR hood, turn on the UV light for 30 minutes.

4.1.6) Place a 12 well plate and a 20 mL syringe in −20° C. for 10 minutes, or until ready to continue. Note: Keep all materials cold until ready to use. The increase in temperature induces premature collagen fibrillogenesis.

4.1.7) Spray all tubes and well plates that are going to be in the hood with 70% ethanol and let them dry for sterilization. Place a 20 mL syringe on ice to cool for later use.

4.1.8) In the PCR hood, open the stainless steel molds to release the BSA rubber and using a scalpel, cut the exhaust channels of the BSA rubber mold.

4.1.9) Under the PCR hood, open the sterile collagen tubes and add 1 mL of the HEPES-MEM solution (make sure that before extracting the HEPES-MEM solution, that it is well mixed and there are no solid deposits).

4.1.10) Using the sterile spatula, thoroughly mix the collagen and buffer solution.

4.1.11) Close and vortex it quickly to ensure a well-mixed hydrogel.

4.1.12) Transfer to a cold 20 mL syringe.

4.1.13) With one hand, hold the BSA Rubber inside of the well and, using the other, dispense half of the collagen hydrogel solution onto the bottom of the well.

4.1.14) Using the sterile tweezers, ensure that the rubber inflow and outflow ends are touching the sides of the well.

4.1.15) Pour collagen solution on top of the rubber until is completely covered.

4.1.16) Ensure that the BSA rubber is suspended within the collagen and that there are no bubbles, especially near the ends of the rubber.

4.1.17) Place the cover and wrap parafilm around the circumference of the well.

4.1.18) Put in the incubator for 1 hr at 37° C. Keep the PCR UV light on.

4.2) After the polymerization of the collagen, UV crosslink the hydrogel via the following procedure. Note: The crosslinking of the collagen will be done using a UV crosslinker apparatus in which the amount of energy can be controlled.

4.2.1) Turn on the UV crosslinker and use the energy setting to irradiate the empty chamber with 630,000 μJ/cm$^2$.

4.2.2) Remove the gels from the incubator.

4.2.3) Spray hands with ethanol, and, inside the chamber, remove the lid as quickly as possible.

4.2.4) Close the chamber and UV crosslink the hydrogels by selecting the energy setting and irradiating 630,000 μJ/cm$^2$.

4.2.5) After the crosslinking cycle, turn off the UV light on the PCR hood 4.2.6) Spray hands with ethanol and open the chamber, quickly placing the lid back onto the well plate. Move the well plate to the PCR hood.

4.2.7) Using the sterile spatula, gently loosen and remove the gel from the well. Flip the gels under the hood to crosslink the bottom of the hydrogel. Repeat step 6.2.3 and 6.2.4.

5) Enzyme Digestion of the BSA Rubber 5.1) In order to have a hollow collagen scaffold, remove BSA Rubber in a way that does not affect the dimensions embedded in the hydrogel. The procedure is described below.

5.1.1) Turn on the UV light for 20-30 min to sterilize the tissue culture hood.

5.1.2) Make 0.25% trypsin solution pH 7.8. For example, for 15 mL of water, add 0.0376 g of trypsin in a 50 mL conical tube. Adjust the pH to 7.8 by adding small amounts (2-5 μL) of 1 M NaCl. Place the solution in a 20 mL syringe and capped with a 0.20 μm syringe filter. Press the plunger to expel liquid through filter and collect the sterile solution in a new tube.

5.1.3) Turn on the water bath and set the temperature to 30° C.

5.1.4) After 30 minutes, turn off the UV light. Spray ethanol on all the tubes and materials that will be used in the hood.

5.1.5) Transfer the collagen hydrogel under the hood and place in separate conical tube.

5.1.6) Add around 3-5 mL (just enough to cover the gels) of 0.25% trypsin solution with a pH of 7.8 to each tube. 5.1.7) Seal the tubes with parafilm and vortex lightly for approximately 1 min.
5.1.8) Place in the 30° C. water bath for 15-24 hr. While in the water bath, lightly vortex the gels frequently until the BSA rubber has been digested or removed from the hydrogel.
Note: In order to determine if the BSA rubber has been removed, either the rubber is floating in the trypsin solution or there are broken-down pieces. There must be no visual dark areas within the hydrogel.
5.2) To ensure that all the BSA rubber and trypsin has been removed from the hydrogels, rinse it as described below.
5.2.1) Turn on the PCR hood UV light for 20-30 min.
5.2.2) Prepare Mosconas solution. Combine potassium chloride (KCl, 28.6 mM), (NaHCO$_3$, 11.9 mM), glucose (9.4 mM) and (NaH$_2$PO$_4$, 0.08 mM) in water. Adjust pH to 7.4 with 1 M NaOH or 12 M HCl solution. Place the solution in a 20 mL syringe and use a syringe filter of 0.20 μm to sterilize the solution.
5.2.3) Spray everything with ethanol prior placing them on the hood and allow the ethanol to dry.
5.2.4) Open the tubes under the hood and transfer the collagen to new sterile conical tubes.
5.2.5) Add 5-10 mL of sterile Mosconas solution (just enough to cover them) and leave in the shaker in the fridge at 4° C. for 30 min.
5.2.6) Aspirate the Mosconas solution and repeat step 7.2.5 twice.
5.2.7) Store at 4° C.
Representative Results:
The results demonstrate that this biofabrication technique is efficient in generating 3D scaffolds that can mimic the spatial arrangement seen in in vivo tissue. The architectural features are vital parameters for tissue engineering application, playing a crucial role in the in vivo cell interaction and functionality of the tissue.

The consistency and mixability of the BSA rubber was an important parameter in producing a BSA rubber that is homogeneous and is able to maintain its intended shape. The solubility of proteins is determined by intermolecular effects, such as the protein—protein interaction, and the interaction with the solvent, which induces changes on the overall protein behavior. The conductivity of the BSA solution was measured, which is an indication of the salt concentration of the solutions. As expected, the samples that had the highest conductivity (2×PBS solvent) facilitated the solubility of the BSA.

Another parameter used to determine the appropriate condition for the development of this sacrificial material was the reaction rate. The reaction time of the BSA decreased as the concentration of glutaraldehyde increased, as expected. The fixative reacts with the α-amino groups of the amino acids, the N terminal amino group of peptides, and the sulfhydryl group of cysteine. The glutaraldehyde reacts predominantly with the BSA through the amino groups of lysine to form the intermolecular covalent bonds (FIG. 1A)[14]. After an incubation period, the samples showed a color change from pale yellow to dark yellow and brown, increasing in intensity with increased glutaraldehyde concentration (FIG. 1B). The 20%, 30%, and 40% BSA with 2% glutaraldehyde in water did not form a rubber. The 40% BSA solution, due to its high viscosity and the highly reactive fixative, resulted in varying strength along the rubber. This behavior can be caused by the difficulty of the glutaraldehyde in penetrating the protein chains homogeneously. The solvent greatly influenced the solubility of the protein as well as its reaction with the fixative. The 2×PBS solutions were easily mixable. The BSA solution with water was difficult to mix. BSA solubility is greatly affected by the conductivity of the solvent, causing conformational changes in the protein. The most promising samples were the 30% BSA with 3% glutaraldehyde in 1×PBS and 2×PBS.

To ensure that the rubber was able to sustained loading forces, a compression test was performed. The mechanical properties of four samples of BSA rubber were measured: 30% BSA 3% glutaraldehyde in 2×PBS, 30% BSA 3% glutaraldehyde in 1×PBS, 20% BSA 3% glutaraldehyde in 2×PBS and 20% BSA 2% glutaraldehyde in 1×PBS. The sine waves showed a very small phase change between the load and displacement curves that are transferred to the stress and strain curves. Based on the stress and strain curves, the first three samples showed hysteresis in between loading and unloading. These three specimens behaved as a viscoelastic material that contains elastic and viscous properties when forces were applied. The 20% BSA 2% glutaraldehyde showed signs of permanent deformation. The 30% BSA 3% glutaraldehyde in 1×PBS and 2×PBS showed a similar behavior. The elastic modulus was determined from the linear portion of these four samples. The concentration of the phosphate solvent significantly increased the elastic modulus at the range tested (p=0.03). The 20% BSA 2% glutaraldehyde in 1×PBS deformed easily, showing a lower elastic modulus.

To evaluate the enzymatic digestion of the rubber, the reaction rate was calculated based on the disappearance of the BSA rubber when placed in contact with the enzyme at specific time point. The enzymatic digestion process was treated as a batch reactor. A comparison between the starting rubber concentration prior to treatment and the rubber left after being lyophilized was made to obtain the kinetics of the digestion. The rate of reaction for each sample was studied in relation to the concentration of glutaraldehyde and BSA, solvent, and the residence time. A clear trend was observed between the crosslinker concentrations and the reaction rate of dissociation of the entity. Statistical analysis was performed at each time point. For the 15-hr time point, the glutaraldehyde concentration significantly affected the reaction rate resulting in a p value of 0.02. After that time point, both the glutaraldehyde and the BSA concentration significantly affected the rate. The most influential factor overall was the glutaraldehyde concentration, indicated by a more significant p value. The increase in glutaraldehyde concentration decreased the reaction rate of the digestion of the rubber entity.

The amount of protein dissolved by trypsin was determined using a BCA assay. A common trend was observed: the lower the concentration of the fixative, the more protein was digested from the BSA rubber. Trypsin interacted with the rubber sample by cleaving the BSA and the newly created covalent bonds formed by the glutaraldehyde, thus dissolving the overall structure over time. It seems that with the 1×PBS there is more solubilized protein at an earlier time point compared to the 2×PBS. Over time, there is an increase of proteins in solution at 15 hr, which continued to increase until 48 hr and then it decreased. This might be due to the trypsin constantly cleaving the proteins and, thus, creating smaller peptides and amino acids. It can also be attributed to the assay's limitations, which can only read peptides that are composed of three or more amino acids. Statistical analysis showed that the BSA and glutaraldehyde concentration significantly affected the release of the protein from the BSA rubber (p<0.05). An increase in BSA concentration caused an increase of protein in the supernatant, while an increase in glutaraldehyde caused a decrease in dissolved protein.

To measure the dissociation of this sacrificial material, the rubber was weighed (wet basis) before placing it in contact with the trypsin. The equivalent of dry weight of the rubber placed in the enzyme digestion solution was determined. The enzyme solution reacted with the BSA rubber, and thus, solubilized the protein. The rubber remaining after the treatment was lyophilized overnight and weighed. The solvent influenced the dissociation of the rubber. At the same concentration of BSA and glutaraldehyde, the 2×PBS solvent rubbers retained more of their material compared to the 1×PBS.

Three solid mold pieces were fabricated: Loop Mold, Stability Piece, and Y Mold. The stainless steel Y mold piece was created using the Microlution machine. This mold was reaction injected with 30% BSA and 3% glutaraldehyde in 2×PBS. The rubber was allowed to react overnight at 4° C. The rubber was casted with collagen and then enzyme digested. Preliminary data suggested that at pH 7.8 and a temperature of 30° C. for 15 hr, the BSA rubber can be digested with minimal impact on the collagen scaffold. After 15 hr, the rubber is weakened by the enzyme and loose enough that it leaves the channels without affecting the geometrical features of the collagen. A 3D collagen scaffold was created that has specific geometrical features. A 4 mm diameter channel inside a collagen hydrogel after enzyme digestion of the BSA rubber. The channel was measured with a caliper to ensure that the original dimension was maintained. Indeed, the new channel in the collagen hydrogel was 4 mm. The BSA rubber molds can hold dimensions as small as 300 μm, which was tested using the stability mold. These scaffolds were tested for residual glutaraldehyde and we found no residue after the Mosconas washes.

Conclusion: Several combinations of BSA and glutaraldehyde concentrations were tested using a variety of solvents. This material was created by the reaction between BSA and glutaraldehyde. BSA rubber can be reaction injected into the intricate geometries of the tissue molds. Crosslinked BSA is trypsin labile and readily digested by the enzyme at mild pH and temperature conditions. Conversely, intact type I collagen is very resistant to trypsin digestion. These features were capitalized to selectively remove the BSA rubber leaving the collagen behind. The present work consisted of determining the ideal parameters needed to obtain a labile mold that can deliver specific architectural features to a biocompatible scaffold. The specific features that were evaluated included mixability, enzyme digestion, load bearing, and ability to be reaction injected into a negative mold. The combination of 30% BSA and 3% glutaraldehyde fulfills these requirements. This protocol provides the necessary guidelines to create these three-dimensional scaffolds. The prototype includes a collagen scaffold that represents a branched architecture with one inflow and two outflow channel with diameters of 4- and 3-mm, respectively. This technique has the potential to mimic macro- and micro-environments of the tissue of interest. This technology provides a viable technique to deliver a specific geometrical instructive to a biodegradable material in a relatively easy and timely matter with high fidelity, which can be tuned to mimic the in vivo tissue elasticity and other characteristics of the tissue of interest.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming an engineered bio-scaffold comprising: filling a mold with an albumin rubber such that the albumin rubber conforms to the shape of the mold; removing the albumin rubber from the mold to form a rubber blank; coating the rubber blank with collagen such that the collagen takes the shape of the rubber blank; and selectively dissolving the rubber blank from the inside of the collagen using an enzyme to form the bio-scaffold, wherein the enzyme selectively dissolves the material of the rubber blank while leaving the collagen and forming flow channels inside the bio-scaffold.

2. The method as in claim 1, wherein the enzyme comprises trypsin.

3. The method as in claim 1, wherein the enzyme is provided in a solution having a pH of about 7 to about 9.

\* \* \* \* \*